United States Patent
Wagner et al.

(10) Patent No.: US 7,504,528 B2
(45) Date of Patent: Mar. 17, 2009

(54) MEROCYANINE DERIVATIVES FOR COSMETIC USE

(75) Inventors: Barbara Wagner, Lörrach (DE); Thomas Ehlis, Freiburg (DE); Stefan Müller, Weil am Rhein (DE)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 457 days.

(21) Appl. No.: 10/582,748

(22) PCT Filed: Dec. 8, 2004

(86) PCT No.: PCT/EP2004/053327

§ 371 (c)(1), (2), (4) Date: Jun. 14, 2006

(87) PCT Pub. No.: WO2005/058269

PCT Pub. Date: Jun. 30, 2005

(65) Prior Publication Data

US 2008/0124285 A1    May 29, 2008

(30) Foreign Application Priority Data

Dec. 17, 2003  (EP) .................. 03104746
May 17, 2004  (EP) .................. 04102155

(51) Int. Cl.
| | |
|---|---|
| C07C 255/00 | (2006.01) |
| A61K 8/00 | (2006.01) |
| A61K 8/18 | (2006.01) |
| A61K 8/49 | (2006.01) |
| A61K 31/13 | (2006.01) |
| A61K 31/16 | (2006.01) |
| A61Q 17/04 | (2006.01) |
| A01N 33/00 | (2006.01) |
| A01N 33/02 | (2006.01) |

(52) U.S. Cl. .................. 558/303; 424/59; 424/70.9; 514/579; 514/660

(58) Field of Classification Search .................. None
See application file for complete search history.

(56) References Cited

U.S. PATENT DOCUMENTS

| | | | |
|---|---|---|---|
| 4,212,823 A | 7/1980 | Müller | 260/571 |
| 4,749,643 A | 6/1988 | Öhlschläger et al. | 430/512 |
| 4,891,212 A | 1/1990 | Gosciniak et al. | 424/59 |
| 5,945,091 A | 8/1999 | Habeck et al. | 424/59 |
| 6,037,487 A | 3/2000 | Habeck et al. | 558/449 |
| 6,407,247 B1 | 6/2002 | Habeck et al. | 546/312 |
| 6,787,147 B1 | 9/2004 | Huner et al. | 424/401 |

FOREIGN PATENT DOCUMENTS

WO    2004/006878    1/2004

OTHER PUBLICATIONS

G. V. Kondrat' eva et al., Bulletin of the Academy of Sciences of the USSR Division, pp. 609-614, XP001166946, (1967).
Database Chemcats, ACS, Accession No. 2001:2069196, XP002319526, (Apr. 23, 2003).
Database Registry, ACS, Registry No. 500707-74-4, XP002319527, (Mar. 26, 2003).
Sheryl J. Hays, Journal of Labelled Compounds and Radiopharmaceuticals, vol. 24, No. 4, pp. 351-360, XP001154221, (1986).
Valerio Bertolasi et al., Acta Crystallographica Section B, vol. 54, No. 1, pp. 50-65, XP001166947, (1998).
Chemical Abstracts, vol. 62, No. 9, Abstract No. 10348b, XP002282571, (1965).
R. H. McDougall et al., J. Chem. Soc. C, pp. 2044-2051, XP001189527, (1969).
Database Registry, ACS, Registry No. 353268-63-0, XP002319528, (Aug. 28, 2001).
Database Registry, ACS, Registry No. 500884-77-5, XP002319529, (Mar. 28, 2003).
Database Registry, ACS, Registry No. 395660-48-7, XP002319530, (Feb. 26, 2002).
Database Registry, ACS, Registry No. 395073-64-0, XP002319531, (Feb. 25, 2002).
Database Registry, ACS, Registry No. 353268-66-3, XP002319532, (Aug. 28, 2001).
Database Registry, ACS, Registry No. 385381-05-5, XP002319533, (Jan. 22, 2002).
Balkrishna H. Iyer, J. Indian Inst. Sci., Sect. A, vol. 21, pp. 65-75, XP001166949, (1938).

*Primary Examiner*—Johann R Richter
*Assistant Examiner*—Luke E Karpinski
(74) *Attorney, Agent, or Firm*—Tyler A. Stevenson

(57) ABSTRACT

Described are merocyanine derivatives of formula (1a) or (1b) wherein n and o are integers from 2 to 4 and aminocyclohexenone intermediates. They are used in protecting human and animal hair and skin from UV radiation.

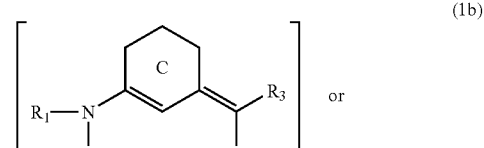

(1b)

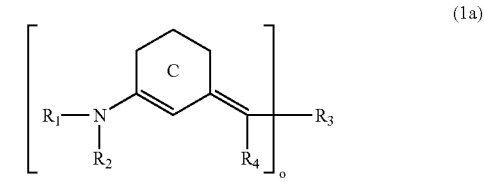

(1a)

11 Claims, No Drawings

OTHER PUBLICATIONS

Database Registry, ACS, Registry No. 20679-36-1, XP002319534, (Nov. 16, 1984).
Database Chemcats, ACS, Accession No. 2001:944037, XP002282574, (Nov. 15, 2001).
Database Chemcats, ACS, Accession No. 2003:1567400, 1567400, (Jan. 1, 2004).
Database Chemcats, ACS, Accession No. 2004:440894, (Jan. 1, 2004).
Database Chemcats, ACS, Accession No. 2003:1567486, (Jan. 1, 2004).

MEROCYANINE DERIVATIVES FOR COSMETIC USE

The present invention relates to the use of merocyanine derivatives in protecting human and animal hair and skin from UV radiation and to cosmetic compositions comprising such compounds.

The compounds for use in accordance with the invention correspond to formula

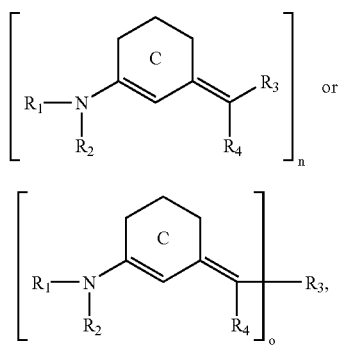

wherein
$R_2$ is hydrogen; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl; or a cyano group;
$R_4$ is a cyano group; or -$Q_1$-$R_5$;
$Q_1$ is —COO—; —CONH—; —CO—; —SO$_2$—; or —CONR$_6$—;
$R_5$ is $C_1$-$C_{22}$alkyl; cyclo-$C_3$-$C_8$alkyl; or unsubstituted or $C_1$-$C_6$alkyl-substituted $C_6$-$C_{20}$aryl;
$R_6$ is hydrogen; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl;
the cyclohexene radical C is not substituted or substituted by one or more $C_1$-$C_5$alkyl;
n is from 2 to 4;
o is from 2 to 4;
if n=2, in formula (1a)
$R_1$ is an alkylene, cycloalkylene or phenylene-radical; or $R_1$ and $R_2$ simultaneously form an alkylene, cycloalkylene or phenylene radical; and
$R_3$ is a cyano group; or -$Q_1$-$R_5$; or $R_3$ and $R_4$ together form a 5- to 7-membered, monocyclic carbocyclic ring, which is optionally interrupted by —O— or —NR$_7$—;
If o=2, in formula (1b)
$R_3$ is an alkylene, cycloalkylene or phenylene radical, which is optionally substituted with $C_1$-$C_4$alkyl, $C_1$-$C_4$alkoxy, —COR$_6$, —COOR$_6$ or —CONHR$_6$; and
$R_1$ is hydrogen; a cyano group; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl; or $R_1$ and $R_2$ together with the nitrogen atom linking them form a —(CH$_2$)$_m$— ring which is optionally interrupted by —O— or by —NR$_7$—;
$R_7$ is hydrogen; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl;
m is a number from 3 to 7;
if n=3, in formula (1a)
$R_1$ is a trivalent alkyl group, which is optionally interrupted by one or more —O— or —NR$_7$-groups; and
$R_3$ is a cyano group; or -$Q_1$-$R_5$; or $R_3$ and $R_4$ together form a 5- to 7-membered, monocyclic carbocyclic ring;
if o=3, in formula (1b)
$R_3$ is an alkylidene, cycloalkylidene or phenylidene radical; and
$R_1$ is hydrogen; a cyano group; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl; or $R_1$ and $R_2$ together with the nitrogen atom linking them form a —(CH$_2$)$_m$— ring which is optionally interrupted by —O— or by —NR$_7$—;
if n=4, in formula (1a)
$R_1$ is a tetravalent alkyl group; and
$R_3$ is a cyano group or -$Q_1$-$R_5$; or $R_3$ and $R_4$ together form a 5- to 7-membered, monocyclic carbocyclic ring;
if o=4, in formula (1b)
$R_3$ is a tetravalent alkyl group; and
$R_1$ is hydrogen; a cyano group; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl; or $R_1$ and $R_2$ together with the nitrogen atom linking them form a —(CH$_2$)$_m$— ring which is optionally interrupted by —O— or by —NR$_7$—.

$C_1$-$C_{22}$Alkyl denotes a linear or branched, unsubstituted or substituted alkyl group such as, for example, methyl, ethyl, propyl, isopropyl, n-butyl, n-hexyl, cyclohexyl, n-decyl, n-dodecyl, n-octadecyl, eicosyl, methoxyethyl, ethoxypropyl, 2-ethylhexyl, hydroxyethyl, chloropropyl, N,N-diethylaminopropyl, cyanoethyl, phenethyl, benzyl, p-tert-butylphenethyl, p-tert-octyl-phenoxyethyl, 3-(2,4-di-tert-amylphenoxy)-propyl, ethoxycarbonylmethyl-2-(2-hydroxy-ethoxy)ethyl or 2-furylethyl.

$C_1$-$C_6$alkoxy denotes methoxy, ethoxy, n-propoxy, isopropoxy, n-butoxy, sec-butoxy, tert-butoxy, amyloxy, isoamyloxy or tert-amyloxy.

$C_6$-$C_{10}$aryl denotes, for example, phenyl, tolyl, anisyl, mesityl, chlorophenyl, 2,4-di-tert-amylphenyl and naphthyl.

Heterocyclic radicals contain one, two, three or four identical or different ring hetero atoms. Special preference is given to heterocycles which contain one, two or three, especially one or two, identical or different hetero atoms. The heterocycles may be mono- or poly-cyclic, for example mono-, bi- or tri-cyclic. They are preferably mono- or bi-cyclic, especially mono-cyclic. The rings preferably contain 5, 6 or 7 ring members. Examples of monocyclic and bicyclic heterocyclic systems from which radicals occurring in the compounds of formula (1a) and (1b) may be derived are, for example, pyrrole, furan, thiophene, imidazole, pyrazole, 1,2,3-triazole, 1,2,4-triazole, pyridine, pyridazine, pyrimidine, pyrazine, pyran, thiopyran, 1,4-dioxane, 1,2-oxazine, 1,3-oxazine, 1,4-oxazine, indole, benzothiophene, benzofuran, pyrrolidine, piperidine, piperazine, morpholine and thiomorpholine.

When $R_5$ and $R_6$ together form a 5- to 7-membered monocyclic carbocyclic or heterocyclic ring, such a ring is, for example, a 1,3-dioxocyclohexane ring such as, for example, a dime-done ring, a 1,3-dioxo-5,5-diethylcyclohexane ring, a 1,3-diaza-2,4,6-trioxocyclohexane ring such as, for example, a barbituric acid ring, a 1,3-dimethylbarbituric acid ring, a 1-phenylbar-bituric acid ring, a 1-methyl-3-octylbarbituric acid ring, a 1-ethyl-3-octyloxycarbonylethyl-barbituric acid ring, a 1,2-diaza-3,5-dioxocyclopentane ring such as, for example, a 1,2-diaza-1,2-dimethyl-3,5-dioxocyclopentane ring, a 1,2-diaza-1,2-diphenyl-3,5-dioxocyclopentane ring, or a 2,4-diaza-1-alkoxy-3,5-dioxocyclohexene ring such as, for example, a 2,4-diaza-1-ethoxy-4-ethyl-3,5-dioxocyclohexene ring, a 2,4-diaza-1-ethoxy-4-[3-(2,4-di-tertamylphenoxy)propyl]-3,5-dioxocyclohexene ring etc.

Preference is also given to compounds of formula (1a) wherein $R_1$ is defined as in formula (1a);
$R_2$ is hydrogen;
$R_3$ is a cyano group;
$R_4$ is —CONHR$_5$; and
$R_5$ is $C_1$-$C_{22}$alkyl; or $C_6$-$C_{20}$aryl.

If in formula (1a) n=2,
preference is further given to the use of compounds of formula

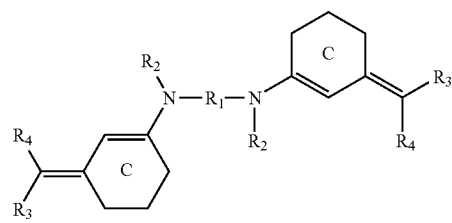

(1c)

are used, wherein
$R_1$ is a *—(CH$_2$)$_m$—* group, not substituted or substituted with one or more than one $C_1$-$C_5$radicals; a bivalent radical of formula

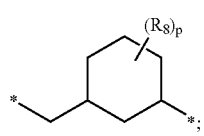

(1a$_1$)

a bivalent radical of formula

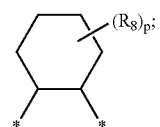

(1a$_2$)

or $R_1$ and $R_2$ together with the 2 linking nitrogen atoms form a bivalent radical of formula (1a$_3$)

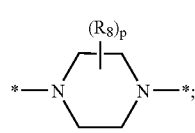

(1a$_3$)

$R_8$ is hydrogen; or $C_1$-$C_5$alkyl;
$R_3$ is a cyano group; or -Q$_1$-R$_5$;
p is a number form 0 to 3;
the cyclohexene radical C is not substituted or substituted by one or more $C_1$-$C_5$alkyl; and
$R_2$, $R_4$, $R_5$, $Q_1$ and m are defined as in formulae (1a) and (1b).

Preference is further given to the use of compounds of formula

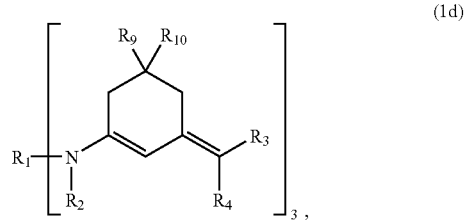

(1d)

wherein
$R_1$ is a trivalent radical of formula

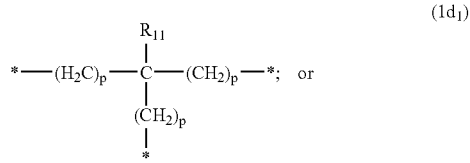

(1d$_1$)

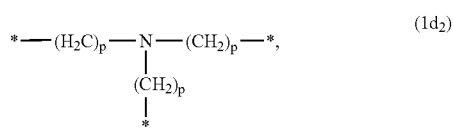

(1d$_2$)

$R_2$ is hydrogen; or $C_1$-$C_5$alkyl;
$R_3$ and $R_4$ independently from each other are a cyano group; or -Q$_1$-R$_5$;
$Q_1$ is —COO—; —CONH—; —CO—; —SO$_2$—; —CONR$_{12}$—;
$R_5$ is $C_1$-$C_5$alkyl;
$R_9$ and $R_{10}$ independently from each other are $C_1$-$C_4$alkyl;
$R_{11}$ and $R_{12}$ independently from each other are hydrogen; or $C_1$-$C_5$alkyl; and
p is a number from 0 to 5.

Preference is further given to the use of compounds of formula

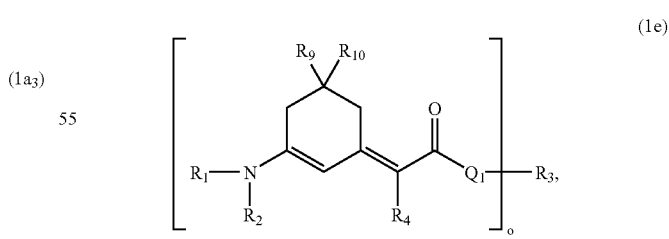

(1e)

wherein
$R_1$ and $R_2$ are each independently of the other $C_1$-$C_{22}$alkyl; or a cyano group; or $R_1$ and $R_2$ together with the nitrogen atom linking them form a —(CH$_2$)$_m$— ring which is optionally interrupted by —O— or by —NR$_7$—;

$R_4$ is a cyano group; or $-Q_1-R_5$;
n is 3; or 4;
if o=3
$R_3$ is a trivalent alkyl radical;
if o=4
$R_3$ is a tetravalent alkyl radical;
$R_5$, $R_7$, $R_9$, $R_{10}$, $Q_1$ and m are defined as in formula (1b).

Further preference is given to the use of momomeric, oligomeric or polymeric compound comprising structural elements of formula

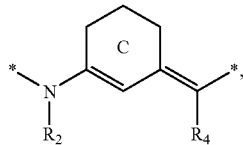

(2)

wherein
at least one of the asterix-marked radicals may be bound to the momomeric, oligomeric or polymeric radical;
the cyclohexene radical C is not substituted or substituted by one or more $C_1$-$C_5$alkyl; and $R_2$ and $R_4$ are defined as in formula (1a) and (1b)
as UV chromophores.

Preferably, momomeric, oligomeric or polymeric compounds correspond to formula

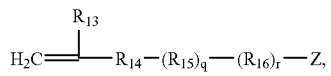

(3)

wherein
Z is a radical of formula (2);
$R_{13}$ is hydrogen; halogen; or $C_1$-$C_5$alkyl;
$R_{14}$ is —CONH—; —COO—; or a phenylene radical;
$R_{15}$ is $C_1$-$C_{20}$alkylene; or $C_6$-$C_{20}$arylene;
$R_{16}$ is —COO—; —OCO—; —CONH—; —NH—CO—O—; —NH—CO—; —SO$_2$NH—; —NHSO$_2$—; —SO$_2$— or —O—;
q is 0; or an integer; and
r is 0; or an integer.

The compounds having structural elements of formula (2) are known and are disclosed for example in U.S. Pat. No. 4,749,643, Representatives of these compounds are the examples 3.1-3.7 in col. 11-13 in this reference.

Representatives of these compounds having structural elements of formula (3) are the examples 2.1-2.9 in col. 11-13 of this reference.

Further compounds for use in accordance with the invention are listed in Table MC1 herein below:

TABLE MC1

| Compound of formula | Structure | $\lambda_{max}$ [nm] |
| --- | --- | --- |
| MC01 | 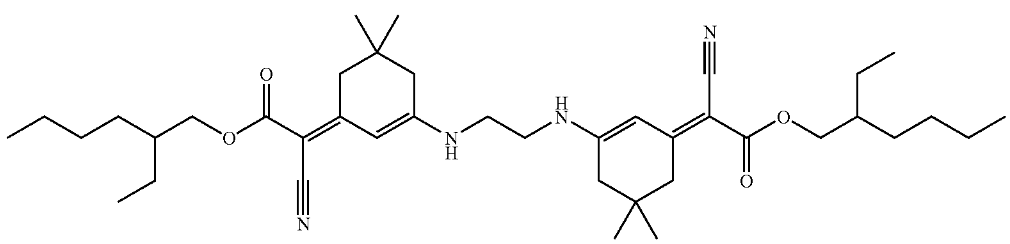 | 366, 398 (EtOH) |
| MC02 | 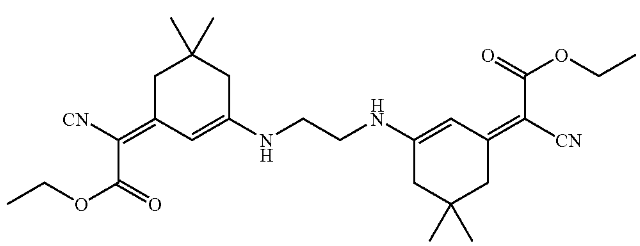 | 366, 398 (EtOH) |
| MC03 | 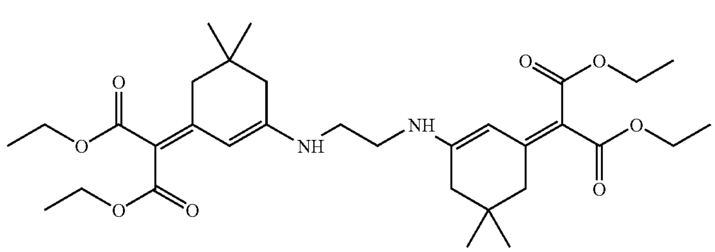 | 383 (EtOH) |

TABLE MC1-continued

| Compound of formula | Structure | $\lambda_{max}$ [nm] |
|---|---|---|
| MC04 | 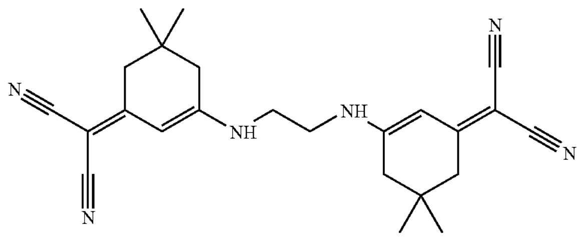 | |
| MC05 | 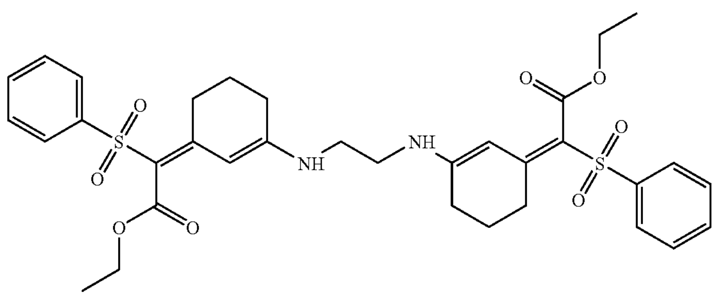 | |
| MC06 | 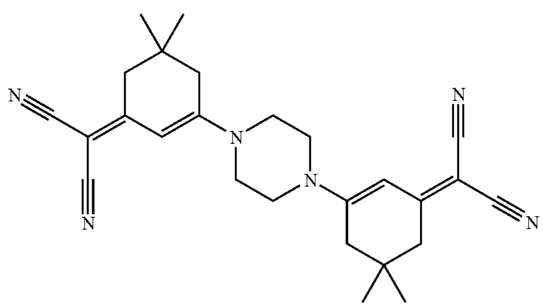 | |
| MC07 | 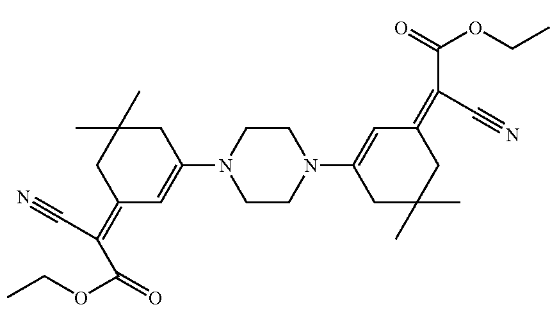 | 406 (EtOH) |

TABLE MC1-continued

| Compound of formula | Structure | $\lambda_{max}$ [nm] |
|---|---|---|
| MC08 | 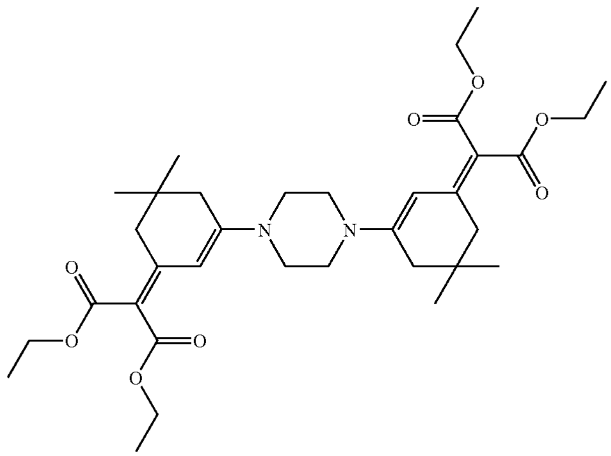 | 373 (EtOH) |
| MC09 | 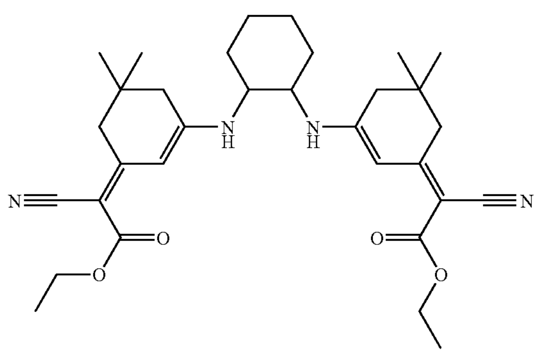 | |
| MC10 | 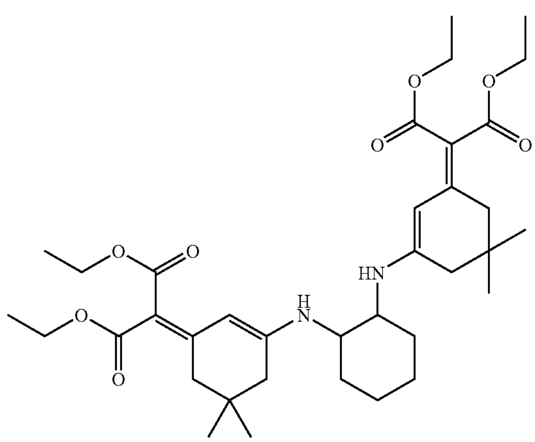 | 384 (EtOH) |

TABLE MC1-continued

| Compound of formula | Structure | $\lambda_{max}$ [nm] |
|---|---|---|
| MC11 | 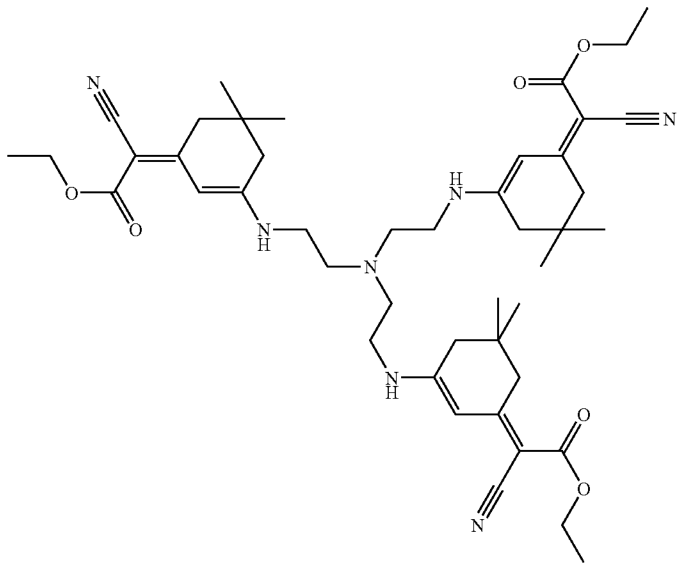 | |
| MC12 | 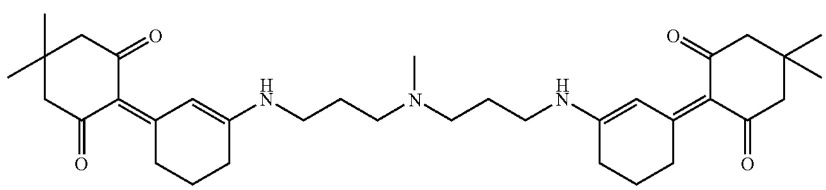 | |
| MC13 | 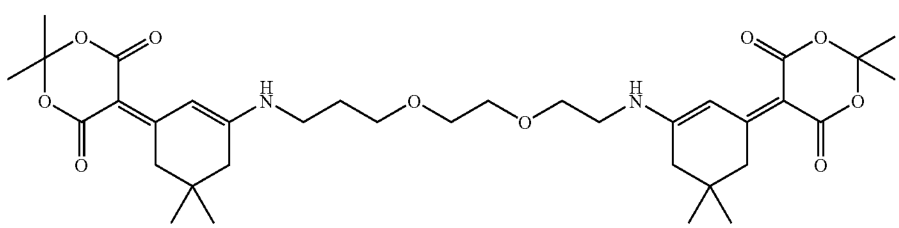 | |
| MC14 | 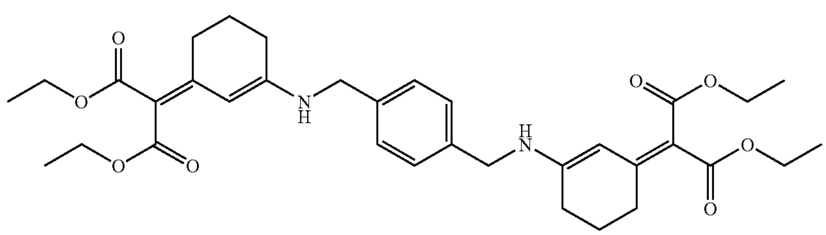 | |
| MC15 | 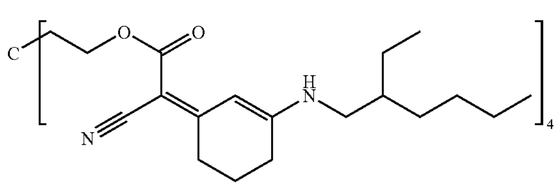 | |

TABLE MC1-continued

| Compound of formula | Structure | $\lambda_{max}$ [nm] |
|---|---|---|
| MC16 | 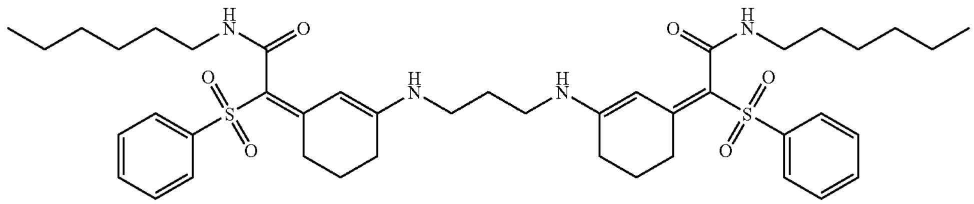 | |
| MC17 | 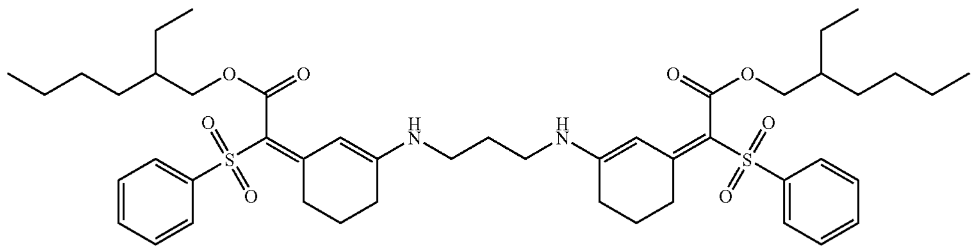 | |
| MC18 | 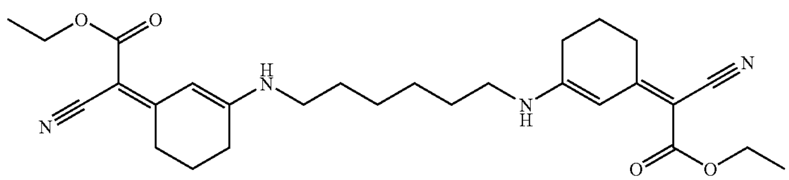 | 388 (EtOH) |
| MC19 | 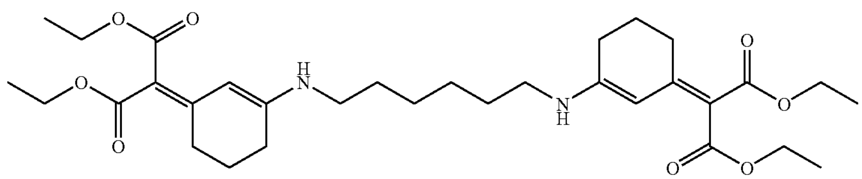 | 370 (EtOH) |
| MC21 | | |
| MC21 | | |

TABLE MC1-continued

| Compound of formula | Structure | $\lambda_{max}$ [nm] |
|---|---|---|
| MC22 | 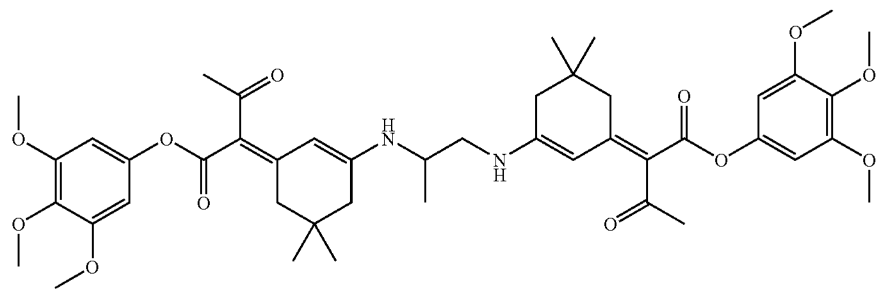 | |
| MC23 | 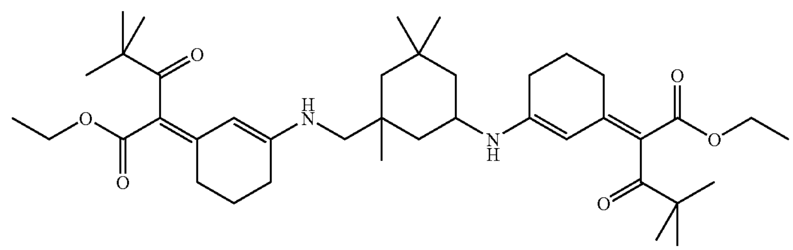 | |
| MC24 | 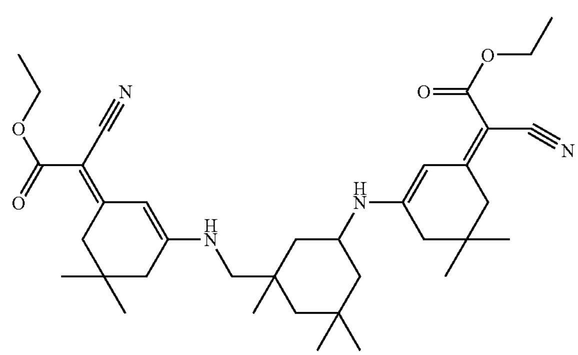 | 391 (EtOH) |
| MC25 | 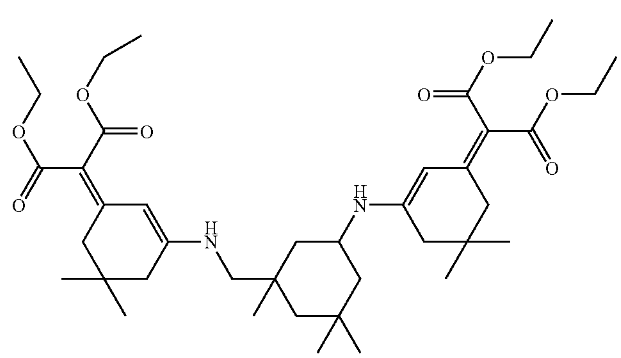 | 378 (EtOH) |

TABLE MC1-continued

| Compound of formula | Structure | $\lambda_{max}$ [nm] |
|---|---|---|
| MC26 | 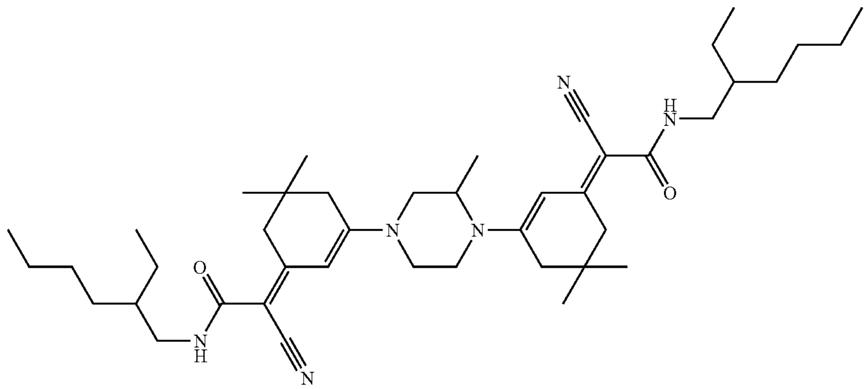 | |
| MC27 | 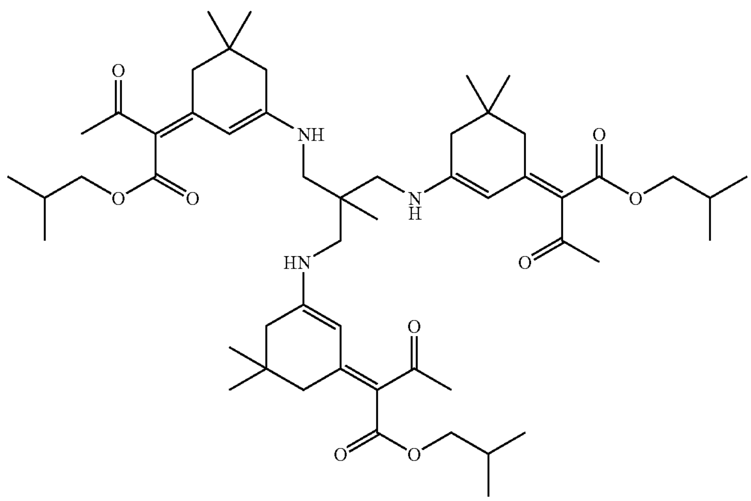 | |
| MC28 | 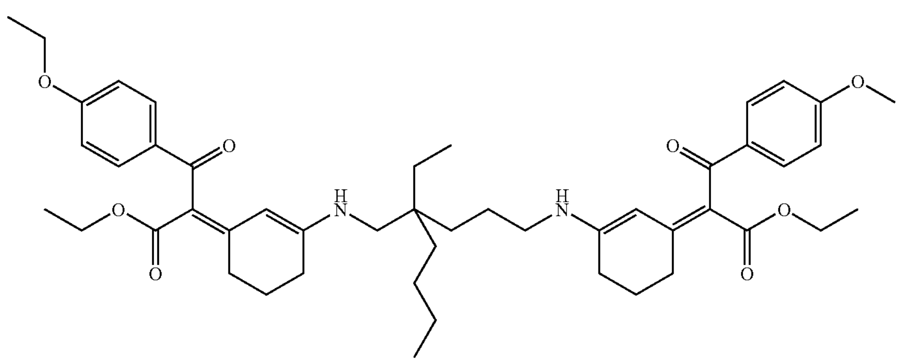 | |
| MC29 | 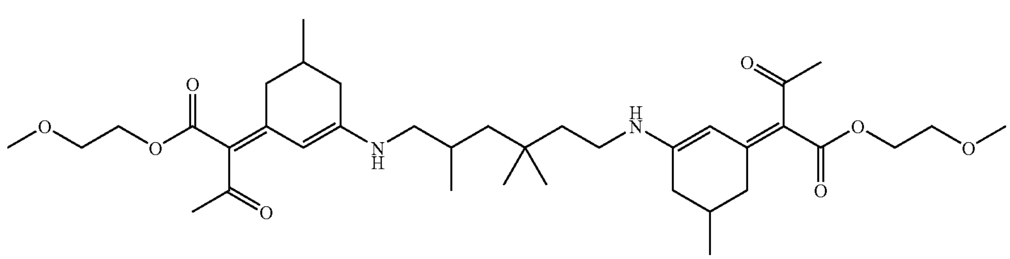 | |

TABLE MC1-continued

| Compound of formula | Structure | $\lambda_{max}$ [nm] |
|---|---|---|
| MC30 | 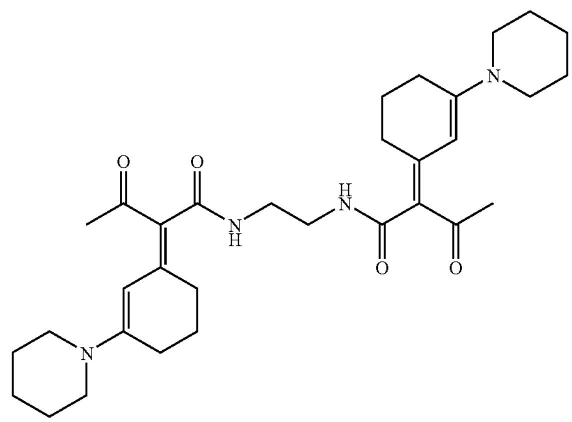 | |
| MC31 | 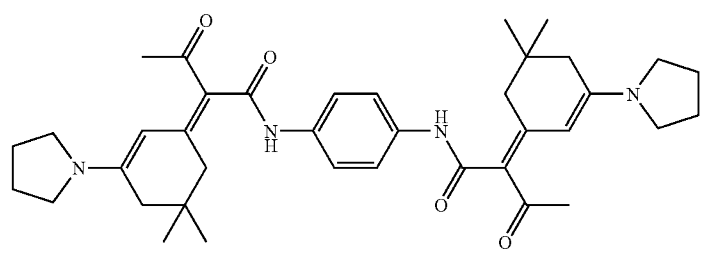 | |
| MC32 | 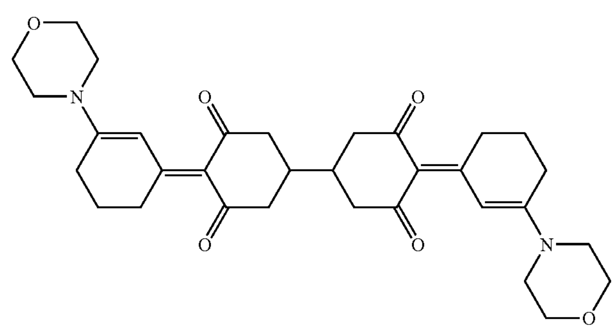 | |
| MC33 | 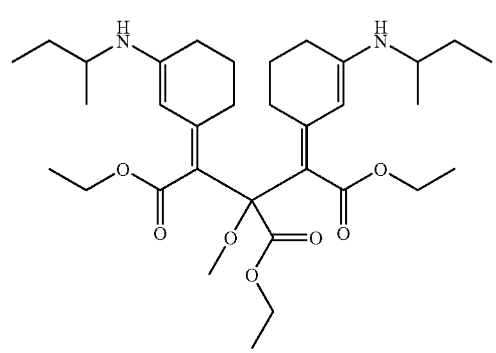 | |

TABLE MC1-continued

| Compound of formula | Structure | $\lambda_{max}$ [nm] |
|---|---|---|
| MC34 | 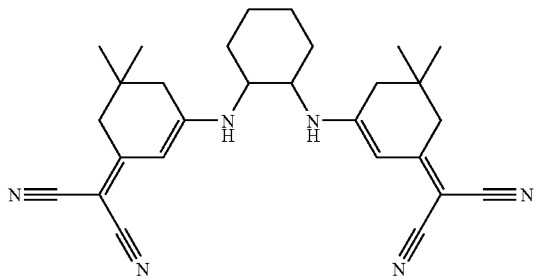 | 357/388 (EtOH) |
| MC35 | 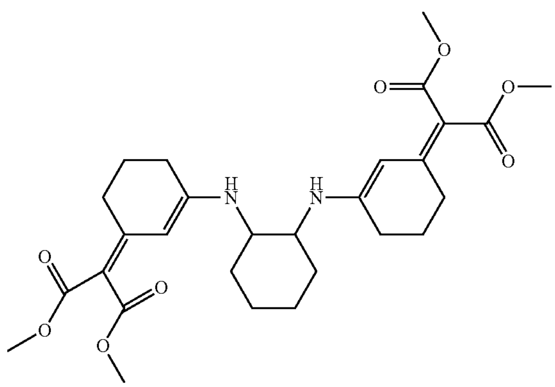 | 389 (EtOH) |
| MC36 | 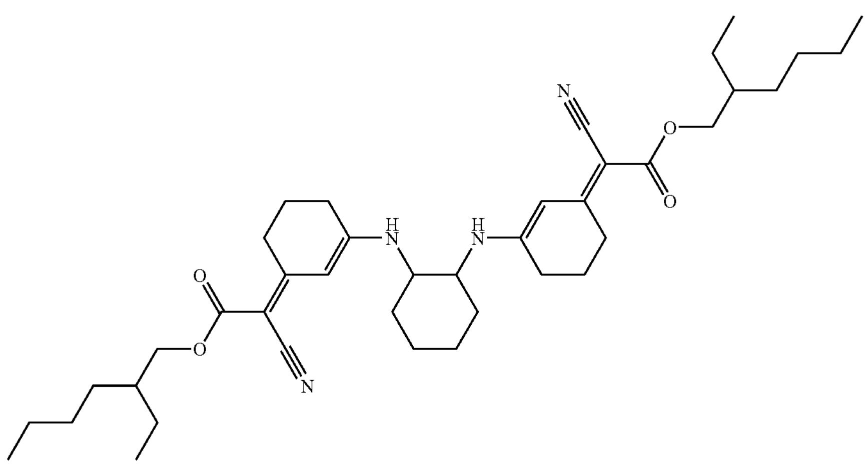 | 401 (EtOH) |
| MC37 | 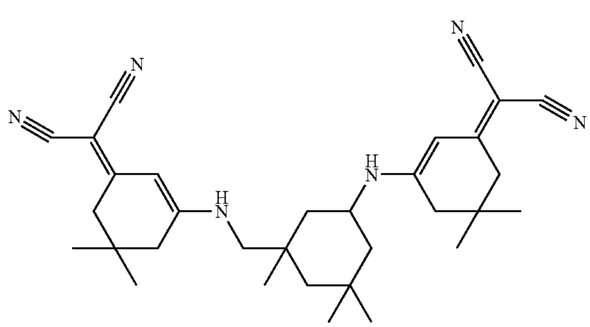 | 383 (Acetonitrile) |

The merocyanine compounds of formula (1a) and (1b) used in accordance with the invention are, in some cases, known compounds but also include novel compounds.

The novel compounds correspond to formula

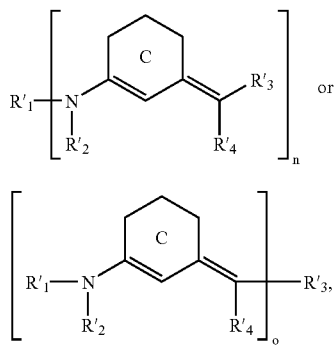

wherein
- $R'_2$ is hydrogen; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl; a cyano group; or $R'_1$ and $R'_2$ together with the nitrogen atom linking them form a —$(CH_2)_m$— ring which is optionally interrupted by —O— or by —$NR'_7$—;
- $R'_4$ is -$Q'_1$-$R'_5$;
- $Q'_1$ is —COO—; —CONH—; —CO—; —$SO_2$—; or —$CONR'_6$—;
- $R'_5$ is $C_1$-$C_{22}$alkyl; cyclo-$C_3$-$C_8$alkyl; or unsubstituted or $C_1$-$C_6$alkyl-substituted $C_6$-$C_{20}$aryl;
- $R'_6$ is hydrogen; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl;
- $R'_7$ is hydrogen; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl;
- the cyclohexene radical C is not substituted or substituted by one or more $C_1$-$C_5$alkyl;
- m is from 3 to 7;
- n is from 2 to 4;
- o is from 2 to 4;
- if n=2, in formula (1'a)
- $R'_1$ is an alkylene, cycloalkylene or phenylene-radical; or $R'_1$ and $R'_2$ simultaneously form an alkylene, cycloalkylene or phenylene radical; and
- $R'_3$ is a cyano group or -$Q'_1$-$R'_5$; or $R'_3$ and $R'_4$ together form a 5- to 7-membered, monocyclic carbocyclic ring;
- If o=2, in formula (1'b)
- $R'_3$ is an alkylene, cycloalkylene or phenylene radical; and
- $R'_1$ is hydrogen; a cyano group; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl; or $R_1$ and $R_2$ together with the nitrogen atom linking them form a —$(CH_2)_m$— ring which is optionally interrupted by —O— or by —$NR'_7$—;
- if n=3, in formula (1'a)
- $R'_1$ is a trivalent alkyl group, which is optionally interrupted by one or more —O— or —$NR'_7$-groups; and
- $R'_3$ is a cyano group or -$Q'_1$-$R'_5$; or $R'_3$ and $R'_4$ together form a 5- to 7-membered, monocyclic carbocyclic ring;
- if o=3, in formula (1'b)
- $R'_3$ is an alkylidene, cycloalkylidene or phenylidene radical; and
- $R'_1$ is hydrogen; a cyano group; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl; or $R'_1$ and $R'_2$ together with the nitrogen atom linking them form a —$(CH_2)_m$— ring which is optionally interrupted by —O— or by —$NR'_7$—;
- if n=4, in formula (1'a)
- $R'_1$ is a tetravalent alkyl group; and
- $R'_3$ is a cyano group or -$Q'_1$-$R'_5$; or $R'_3$ and $R'_4$ together form a 5- to 7-membered, monocyclic carbocyclic ring;
- if o=4, in formula (1'b)
- $R'_3$ is a tetravalent alkyl group; and
- $R'_1$ is hydrogen; a cyano group; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl; or $R'_1$ and $R'_2$ together with the nitrogen atom linking them form a —$(CH_2)_m$— ring which is optionally interrupted by —O— or by —$NR'_7$—.

The preparation of the compounds of formula (1a) and (1b) may be carried out according to known methods of the prior art as described for example in U.S. Pat. No. 4,749,643 on col. 13, line 66-col. 14, line 57 and the references cited therein.

The compounds of formula (1a) can be prepared starting from 1-aminocyclohexanone-3 of the general formula

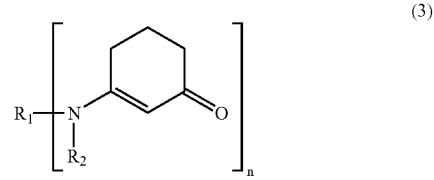

wherein $R_1$, $R_2$ and n are defined as in formula (1a) by condensation of dihydroxyresorcines with primary or secondary amine compounds. After alkylation with dimethylsulfate or other suitable alkylating agents like diethylsulfate and subsequent reaction with a suitable methylene-active compound compounds of formula (1a) are obtained.

The alkylation reaction of the starting compounds of formula (3) with suitable alkylating agents like dimethylsulfate may be carried out in a suitable solvent, preferably dimethylsulfoxide, N-methylpyrrolidone, dimethylformamide or dimethylacetamide. Protic solvents like methanol, ethanol, iso-butanol, tert-butanol or iso-propanol are also suitable. The reaction may also be carried out in aliphatic or aromatic solvents like hexane, toluene or xylol. Ether compounds like diethylether and tetrahydrofurane or halogenated solvents like chloroform or dichlormethane are also suitable solvents as well as mixtures of these solvents.

The reaction may be carried out at temperatures between −80° C. and the boiling point of the reaction mixture, preferably from 60 to 120° C.

The intermediates of formula (3), wherein
- $R_2$ is hydrogen; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl; or $R_1$ and $R_2$ together with the nitrogen atom linking them form a —$(CH_2)_m$— ring which is optionally interrupted by —O— or —$NR_3$—;

$R_3$ is hydrogen; $C_1$-$C_{22}$alkyl; cyclo-$C_3$-$C_8$alkyl; or unsubstituted or $C_1$-$C_6$alkyl-substituted $C_6$-$C_{20}$aryl;
m is from 3 to 7;
n is from 2 to 4;
the cyclohexene radical C is unsubstituted or substituted by one or more $C_1$-$C_5$alkyl;
when n=2,
$R_1$ and $R_2$ simultaneously form an alkylene, cycloalkylene or phenylene radical;
when n=3,
$R_1$ is a trivalent alkyl group, which is optionally interrupted by one or more —O— or —$NR_3$-groups;
when n=4,
$R_1$ is a tetravalent alkyl group which is optionally interrupted by one or more —O— or —$NR_3$-groups;
are novel and are a further subject matter of the present invention.

They are useful intermediates for the preparation of UV absorbers and represent themselves UV-B absorbers for protecting human and animal hair and skin from UV radiation.

Further compounds for use in accordance with the invention are listed in Table MC1a herein below:

TABLE MC1a

| Compound of formula | Structure | $\lambda_{max}$ [nm] |
| --- | --- | --- |
| MC01a | 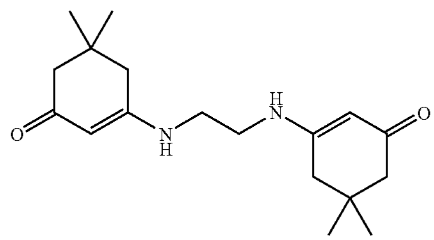 | 296 (EtOH) |
| MC04a | 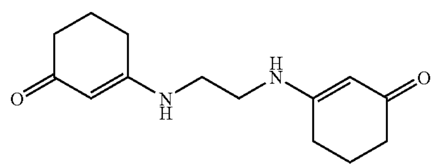 | |
| MC06a | 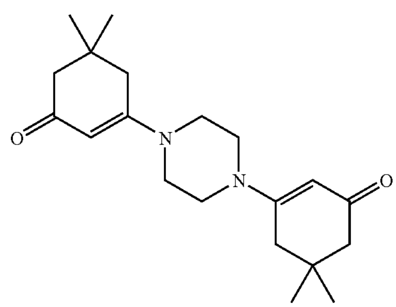 | 309 (EtOH) |
| MC08a | 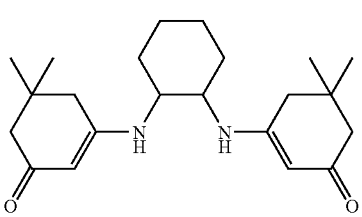 | 295 (Acetonitril) |

TABLE MC1a-continued

| Compound of formula | Structure | $\lambda_{max}$ [nm] |
|---|---|---|
| MC11a | 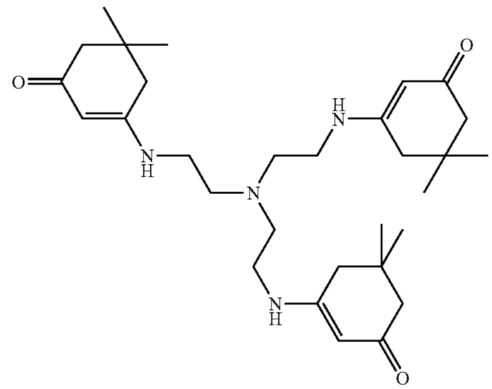 | |
| MC12a | 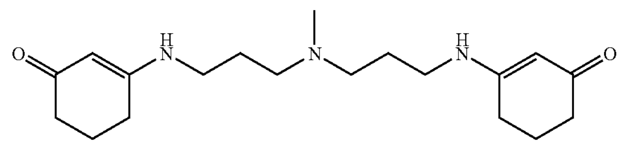 | |
| MC13a | 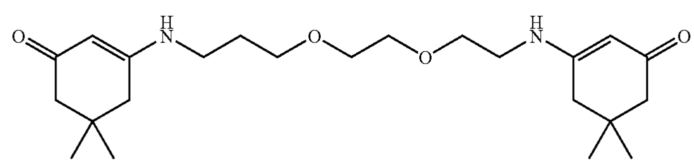 | |
| MC14a | 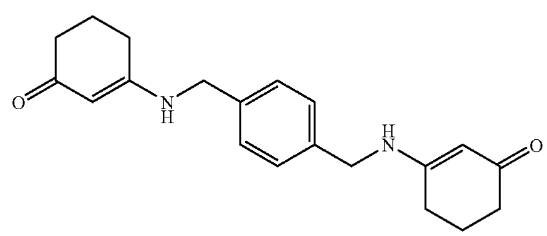 | |

The compounds of the formulae (1a) and (1b) according to the present invention are particularly suitable as UV filters, i.e. for protecting ultraviolet-sensitive organic materials, in particular the skin and hair of humans and animals, from the harmful effects of UV radiation. These compounds are therefore suitable as sunscreens in cosmetic, pharmaceutical and veterinary medical preparations. These compounds can be used both in dissolved form and in the micronized state.

The UV absorbers according to the present invention can be used either in the dissolved state (soluble organic filters, solubulized organic filters) or in the micronised state (nanoscalar organic filters, particulate organic filters, UV-absorber pigments).

The merocyanine derivatives of formula (1a) and (1b) which have no alkyl substituents or only lower-alkyl substituents are characterized by a poor oil-solubility and a high melting point. They are therefore suitable in particular as UV absorbers in the micronized state.

Any known process suitable for the preparation of microparticles can be used for the preparation of the micronised UV absorbers, for example: wet-milling, wet-kneading, spray-drying from a suitable solvent, by the expansion according to the RESS process (Rapid Expansion of Supercritical Solutions), by reprecipitation from suitable solvents, including supercritical fluids (GASR process=Gas Anti-Solvent Recrystallisation/PCA process=Precipitation with Compressed Anti-solvents).

The micronised UV absorbers so obtained usually have an average particle size from 0.02 to 2, preferably from 0.03 to 1.5, and more especially from 0.05 to 1.0 micrometer.

The UV absorbers according to the present invention can also be used as dry substrates in powder form.

The UV absorbers according to the present invention can also be used in specific carriers for cosmetics, for example in solid lipid nanoparticles (SLN) or in inert sol-gel microcapsules wherein the UV absorbers are encapsulated (Pharmazie, 2001 (56), p. 783-786).

The cosmetic formulations or pharmaceutical compositions according to the present invention may additionally contain one or more than one further UV filter.

The cosmetic or pharmaceutical preparations can be prepared by physically mixing the UV absorber(s) with the adjuvant using customary methods, for example by simply stirring together the individual components, especially by making use of the dissolution properties of already known cosmetic UV absorbers, like octyl methoxy cinnamate, salicylic acid isooctyl ester, etc. The UV absorber can be used, for example, without further treatment, or in the micronised state, or in the form of a powder.

Cosmetic or pharmaceutical preparations contain from 0.05-40% by weight, based on the total weight of the composition, of one UV absorber or UV absorber mixtures.

Preference is given to the use of mixing ratios of the UV absorber of formula (1a) and (1b) according to the present invention and optionally further light-protective agents from 1:99 to 99:1, preferably from 1:95 to 95:1 and most preferably from 10:90 to 90:10, based on weight. Of special interest are mixing ratios of from 20:80 to 80:20, preferably from 40:60 to 60:40 and most preferably approximately 50:50. Such mixtures can be used, inter alia, to improve the solubility or to increase UV absorption.

Suitable UV filter substances which can be additionally used with the UV absorbers according to the present invention are for example p-aminobenzoic acid derivatives, for example 4-dimethylaminobenzoic acid 2-ethylhexyl ester; salicylic acid derivatives, for example salicylic acid 2-ethylhexyl ester; benzophenone derivatives, for example 2-hydroxy-4-methoxybenzophenone and its 5-sulfonic acid derivative; dibenzoylmethane derivatives, for example 1-(4-tert-butylphenyl)-3-(4-methoxyphenyl)propane-1,3-dione; diphenylacrylates, for example 2-ethylhexyl 2-cyano-3,3-diphenylacrylate, and 3-(benzofuranyl) 2-cyanoacrylate; 3-imidazol-4-ylacrylic acid and esters; benzofuran derivatives, especially 2-(p-aminophenyl)-benzofuran derivatives, described in EP-A-582 189, U.S. Pat. Nos. 5,338,539, 5,518,713 and EP-A-613 893; polymeric UV absorbers, for example the benzylidene malonate derivatives described in EP-A-709 080; cinnamic acid derivatives, for example the 4-methoxycinnamic acid 2-ethylhexyl ester and isoamyl ester or cinnamic acid derivatives described in U.S. Pat. No. 5,601,811 and WO 97/00851; camphor derivatives, for example 3-(4'-methyl)benzylidene-bornan-2-one, 3-benzylidenebornan-2-one, N-[2(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylenedimethine)-bis(7,7-dimethyl-2-oxo-bicyclo[2.2.1]heptane-1-methanesulfonic acid) and salts, 3-(4'-sulfo)benzylidene-bornan-2-one and salts; camphorbenzalkonium methosulfate; hydroxyphenyltriazine compounds, for example 2-(4'-methoxyphenyl)-4,6-bis(2'-hydroxy-4'-n-octyloxyphenyl)-1,3,5-triazine; 2,4-bis{[4-(3-(2-propyloxy)-2-hydroxypropyloxy)-2-hydroxy]-phenyl}-6-(4-methoxyphenyl)-1,3,5-triazine; 2,4-bis{[4-(2-ethylhexyloxy)-2-hydroxy]-phenyl}-6-[4-(2-methoxyethyl-carboxyl)-phenylamino]-1,3,5-triazine; 2,4-bis{[4-(tris(trimethylsilyloxy-silylpropyloxy)-2-hydroxy]-phenyl}-6-(4-methoxyphenyl)-1,3,5-triazine; 2,4-bis{[4-(2''-methylpropenyloxy)-2-hydroxy]-phenyl}-6-(4-methoxyphenyl)-1,3,5-triazine; 2,4-bis{[4-(1',1',1',3',5',5',5'-heptamethyltrisilyl-2''-methyl-propyloxy)-2-hydroxy]-phenyl}-6-(4-methoxyphenyl)-1,3,5-triazine; 2,4-bis{[4-(3-(2-propyloxy)-2-hydroxy-propyloxy)-2-hydroxy]-phenyl}-6-[4-ethylcarboxy)-phenylamino]-1,3,5-triazine; benzotriazole compounds, for example 2,2'-methylene-bis(6-(2H-benzotriazol-2-yl)-4-(1,1,3,3-tetramethylbutyl)-phenol; trianilino-s-triazine derivatives, for example 2,4,6-trianiline-(p-carbo-2'-ethyl-1'-oxy)-1,3,5-triazine and the UV absorbers disclosed in U.S. Pat. No. 5,332,568, EP-A-517 104, EP-A-507 691, WO 93/17002 and EP-A-570 838; 2-phenyl-benzimidazole-5-sulfonic acid and salts thereof; menthyl o-aminobenzoates; physical sunscreens coated or not as titanium dioxide, zinc oxide, iron oxides, mica, MnO, Fe2O3, Ce2O3, Al2O3, ZrO2. (surface coatings: polymethylmethacrylate, methicone (methylhydrogenpolysiloxane as described in CAS 9004-73-3), dimethicone, isopropyl titanium triisostearate (as described in CAS 61417-49-0), metal soaps as magnesium stearate (as described in CAS 4086-70-8), perfluoroalcohol phosphate as C9-15 fluoroalcohol phosphate (as described in CAS 74499-44-8; JP 5-86984, JP 4-330007)). The primary particle size is an average of 15 nm-35 nm and the particle size in dispersion is in the range of 100 nm-300 nm. aminohydroxy-benzophenone derivatives disclosed in DE 10011317, EP 1133980 and EP 1046391 phenyl-benzimidazole derivatives as disclosed in EP 1167358; the UV absorbers described in "Sunscreens", Eds. N. J. Lowe, N. A. Shaath, Marcel Dekker, Inc., New York and Basle or in Cosmetics & Toiletries (107), 50ff (1992) also can be used as additional UV protective substances.

Preferably, the following UV filter combinations are of special interest:

-UV-filter combinations (T) comprising ($t_1$) at least one merocyanine derivative of formula (1a) or (1b); and ($t_2$) a triazine compound of formula

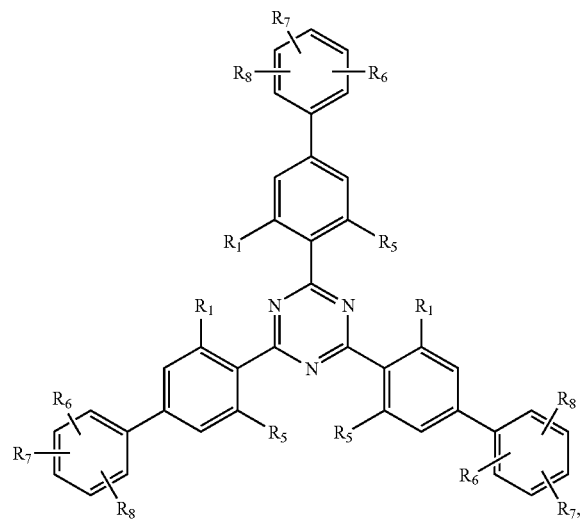

($t_21$)

wherein $R_1$ and $R_5$ are hydrogen; $C_1$-$C_{18}$alkyl; or $C_6$-$C_{12}$aryl; and $R_6$, $R_7$ and $R_8$, independently from each other are hydrogen; hydroxy; halogen; $C_1$-$C_{18}$alkyl; $C_1$-$C_{18}$alkoxy; $C_6$-$C_{12}$aryl; biphenylyl; $C_6$-$C_{12}$aryloxy; $C_1$-$C_{18}$alkylthio; carboxy; —COOM; $C_1$-$C_{18}$-alkylcarboxyl; aminocarbonyl; or mono- or di-$C_1$-$C_{18}$alkylamino; $C_1$-$C_{10}$acylamino; or —COOH.

Most preferred are UV-filter combinations comprising (t₃) the compound of formula (MC02); and (t₄) 1,3,5-Triazine, 2,4,6-tris[1,1'-biphenyl]-4-yl-(9CI).

The compounds of formula (1a) and (1b) may also be used as an anti-wrinkle perception modifier.

The cosmetic or pharmaceutical preparations may be, for example, creams, gels, lotions, alcoholic and aqueous/alcoholic solutions, emulsions, wax/fat compositions, stick preparations, powders or ointments. In addition to the above mentioned UV filters, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight und preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or pharmaceutical compositions/preparations according to the invention may also contain one or one more additional compounds like fatty alcohols, esters of fatty acids, natural or synthetic triglycerides including glyceryl esters and derivatives, pearlescent waxes, hydrocarbon oils, silicones or siloxanes (organosubstituted polysiloxanes), fluorinated or perfluorinated oils, emulsifiers, super-fatting agents, surfactants, consistency regulators/thickeners and rheology modifiers, polymers, biogenic active ingredients, deodorizing active ingredients, anti-dandruff agents, antioxidants, hydrotropic agents, preservatives and bacteria-inhibiting agents, perfume oils, colorants, polymeric beads or hollow spheres as SPF enhancers, Cosmetic or Pharmaceutical Preparations Cosmetic or pharmaceutical formulations are contained in a wide variety of cosmetic preparations. There come into consideration, for example, especially the following preparations: skin-care preparations, bath preparations, cosmetic personal care preparations, foot-care preparations, light-protective preparations, skin-tanning preparations, depigmenting preparations, deodorants, antiperspirants, preparations for cleansing and caring for blemished skin, shaving preparations, fragrance preparations or cosmetic hair-treatment preparations Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection milk and sun protection preparations in the form of a spray.

The cosmetic preparation according to the invention is characterized by excellent protection of human skin against the damaging effect of sunlight.

PREPARATION EXAMPLES

Example 1

Preparation of the Compound MC 20

1a. Preparation of the Preliminary Stage (Compound MC 01a)

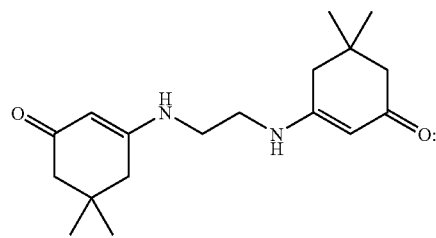

A mixture of 6.04 g ethylenediamine and 31.15 g dimedone in 200 ml toluene is heated under reflux conditions using a water separator for three hours.

After cooling down the mixture the product is filtered off, washed with minor amounts of ethyl acetate and dried in vacuum at 80° C.

The yield is nearly quantitative.

Mp. ≧250° C.

Example 1b

Preparation of the Compound MC2

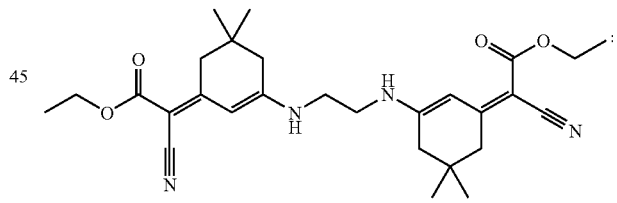

7.61 g of the compound MC14a are dissolved in 375 ml N-methylpyrrolidone at 100° C. and mixed dropwise with 6.50 g dimethylsulfate.

The reaction mixture is stirred for 60 minutes at 100° C.

After cooling down to 80° C. a mixture of 5.81 g cyan acidic acidethylester, 5.14 g triethylamine and 4.3 ml isopropanol is added slowly dropwise. The reaction mixture is stirred at a temperature of 100° C. for 90 minutes.

After cooling down of the reaction mixture the raw product is filtered off.

Subsequent column chromatography with a mixture of toluene and methanol (6:4) over silica gel delivers 1.28 g (10% o. th.) of a pure product which is dried in vacuum at 80° C.

$\lambda_{max}$ (acetonitril)=389 nm.

Example 2a

Preparation of Compound MC06a

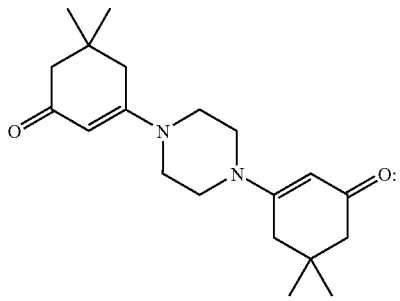

A mixture of 9.06 g dimedone and 2.78 g piperazine in 64 ml toluene is heated under reflux conditions using a water separator for five hours.

After cooling down the mixture the product is filtered off, washed with minor amounts of ethyl acetate and dried in vacuum at 80° C. Yield: 75%.

Example 2b

Preparation of the Compound MC07

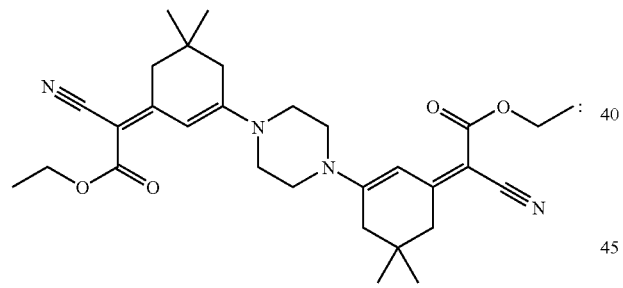

3.34 g dimethylsulfate are added dropwise to 4.33 g of the compound MC 06a (prepared in Example 2a). The reaction mixture is stirred for 60 minutes at 100° C.

After cooling down to 80° C. a mixture of 2.89 g ethyl cyano acetate and 5.21 g of triethylamine is added dropwise.
The reaction mixture is stirred at a temperature of 110° C. for 90 minutes.

After cooling down and the addition of 300 ml water the raw product is filtered off. Subsequent column chromatography with a mixture of toluene and methanol (6:4) over silica gel delivers 4.5 g (65% o. th.) of a pure product, which is dried in vacuum at 80° C.

$\lambda_{max}$ (ethanol)=406 nm.

Example 3a

Preparation of Compound MC08a

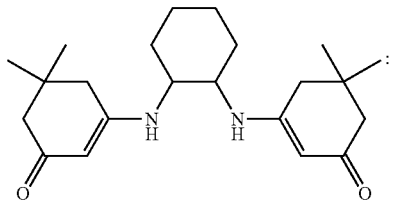

A mixture of 9.06 g dimedone and 4.30 g 1,2-diaminocyclohexane in 64 ml toluene is heated under reflux conditions using a water separator for three hours.

After cooling down the mixture the product is filtered off, washed with minor amounts of ethyl acetate and dried in vacuum at 80° C. yielding 95% product.

Example 3b

Preparation of the Compound MC10

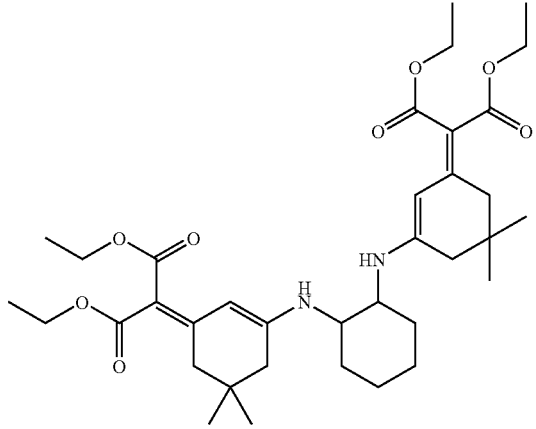

22.86 g of dimethylsulfate are added dropwise to 16.99 g of the compound MC 06a. The reaction mixture is stirred for 60 minutes at 100° C.

After cooling down to 80° C. the mixture is treated with 13.50 g of triethylamine and stirred for 10 minutes. Then a mixture of 16.72 g diethylmalonate and 28.89 g DBU is added slowly dropwise. The reaction mixture is stirred at a temperature of 100° C. for 90 minutes.

After cooling down and the addition of 300 mL of water the raw product is filtered off. Subsequent column chromatography with a mixture of toluene and methanol (6:4) over silica gel delivers 21.28 g (70% o. th.) of a pure product which is dried in vacuum at 80° C.

$\lambda_{max}$ (ethanol)=373 nm.

Example 3c

Preparation of the Compound MC09

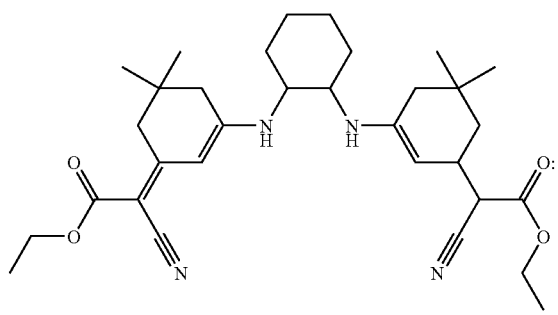

17.93 g (0.05 mol) MC09a are heated with 30 ml dimethylsulfate in an oil bath up to 100° C. and stirred for 40 min at this temperature. The reaction mixture is cooled down to 60° C., a mixture of 11.93 g (0.103 mol) ethyl cyano acetate and 8.25 g (0.120 mol) sodium ethanolate are added in 50 ml ethanol and stirred for 40 minutes at 110° C., wherein ethanol is distilled off during the reaction. The mixture is cooled down, the compound precipitated with $H_2O$ and extracted by suction.

The subsequent column chromatography (Kieselgel) with a 9:1-mixture of toluene and acetone delivers the pure product which is dried in vacuum at 80° C.

Yield: 23.3 g (85% d. Th.).

Example 4

Preparation of Micronized UV Absorbers 100 parts of the compound of formula MC 2 are milled together with zirconium silicate bells (diameter: 0.1 to 4 mm) as grinding aids, a dispersing agent (15 parts of $C_8$-$C_{16}$polyglucoside) and water (85 parts) in a ball mill to a mean particle size of $d_{50}$=200 nm. With this method a micropigment dispersion of a UV absorber is obtained.

APPLICATION EXAMPLES

Example 5

UV-A/UV-B Daily Care UV Protection Lotion

|        | INCI-Name | % w/w (as supplied) |
|--------|-----------|---------------------|
| Part A | Oleth-3 Phosphate | 0.60 |
|        | Steareth-21 | 2.50 |
|        | Steareth-2 | 1.00 |
|        | Cetyl Alcohol | 0.80 |
|        | Stearyl Alcohol | 1.50 |
|        | Tribehenin | 0.80 |
|        | Isohexadecane | 8.00 |
|        | Ethylhexyl Methoxycinnamate | 5.00 |
| Part B | Water | qs to 100 |
|        | Glycerin | 2.00 |
|        | UV-absorber dispersion as described in example 4 | 3.00 |
|        | Disodium EDTA | 0.10 |

-continued

|        | INCI-Name | % w/w (as supplied) |
|--------|-----------|---------------------|
| Part C | Water | 20.00 |
|        | Diazolidinyl Urea (and) Iodopropynyl Butylcarbamate | 0.15 |
|        | Propylene Glycol | 4.00 |
| Part D | Sodium Acrylates Copolymer (and) Paraffinium Liquidum (and) PPG-1 Trideceth-6 | 1.50 |
|        | Cyclopentasiloxane | 4.50 |
|        | PEG-12 Dimethicone | 2.00 |
|        | Tocopheryl Acetate | 0.45 |
|        | Water (and) Citric Acid | qs |
| Part E | Fragrance | qs |

Manufacturing Instruction:

Part A and part B are heated separately to 75° C. Part A is poured into part B under continuous stirring. Immediately after the emulsification, Cyclopentasiloxane and PEG-12 Dimethicone from part D are incorporated into the mixture. Afterwards the mixture is homogenized with an Ultra Turrax at 11 000 rpm for 30 sec. After cooling down to 65° C. Sodium Acrylates Copolymer (and) Paraffinium Liquidum (and) PPG-1 Trideceth-6 are incorporated. Part C is added at a temperature <50° C. At a temperature ≦35° C. Tocopheryl Acetate is incorporated and subsequently the pH is adjusted with Water (and) Citric Acid. At room temperature part E is added.

Example 6

UV Day Lotion

|        | INCI-Name | % w/w (as supplied) |
|--------|-----------|---------------------|
| Part A | Cetyl Phosphate | 1.75 |
|        | C12-C15 Alkyl Benzoate | 5.00 |
|        | Cetearyl Alcohol/PEG-20 Stearate | 2.00 |
|        | Ethoxydiglycol Oleate | 2.00 |
|        | Stearic Acid | 1.50 |
|        | Ethylhexyl Methoxycinnamate | 3.00 |
|        | Isononyl Isononanoate | 2.00 |
| Part B | Aqua | qs to 100 |
|        | Xanthan Gum | 0.35 |
|        | UV-absorber dispersion as described in example 4 | 5.00 |
|        | Disodium EDTA | 0.20 |
|        | Propylene Glycol | 2.00 |
|        | Diazolidinyl Urea (and) Methylparaben (and) Propylparaben (and) Propylene Glycol | 0.70 |
|        | Glycerin | 1.50 |
| Part C | Cyclopentasiloxane (and) Dimethiconol | 1.00 |
|        | Ethoxydiglycol | 3.00 |
|        | Dimethicone | 2.00 |
| Part D | Triethanolamine | qs |

Manufacturing Instruction:

Part A is prepared by incorporating all ingredients, then stirred under moderate speed and heated to 75° C. Part B is prepared and heated to 75° C. At this temperature part B is poured into part A under progressive stirring speed. Then the mixture is homogenized (30 sec., 15000 rpm). At a temperature <55° C. the ingredients of part C are incorporated. The mixture is cooled down under moderate stirring, then the pH is checked and adjusted with triethanolamine.

Example 7

Sun Protection Emulsion

|  | INCI-Name | % w/w (as supplied) |
|---|---|---|
| Part A | Cetearyl Alcohol (and) Dicetyl Phosphate10 (and) Ceteth-Phosphate | 4.00 |
|  | C12-15 Alkyl Benzoate | 2.00 |
|  | Dicaprylyl Ether | 3.00 |
|  | Ethoxydiglycol Oleate | 2.00 |
|  | Stearic Acid | 1.00 |
|  | Ethylhexyl Methoxycinnamate | 3.00 |
|  | Sodium Acrylates Copolymer (and) Glycine1 Soja (and) PPG-Trideceth-6 | 0.30 |
|  | Squalane | 3.50 |
| Part B | Aqua | qs to 100 |
|  | UV-absorber dispersion as described in example 4 | 5.00 |
| Part C | Diazolidinyl Urea (and) Iodopropynyl Butylcarbamate | 0.15 |
|  | Propylene Glycol | 2.50 |
|  | Aqua | 10.00 |
| Part D | Cyclopentasiloxane, Dimethiconol | 2.00 |
|  | Ethoxydiglycol | 5.00 |
|  | Cyclopentasiloxane (and) Dimethicone/Vinyl-dimethicone Crosspolymer | 2.00 |
| Part E | Sodium Hydroxide | 0.10 |

Manufacturing Instruction:

Part A is prepared by incorporating all ingredients, then stirred under moderate speed and heated to 75° C. Part B is prepared and heated to 75° C. At this temperature, part B is poured into part A under progressive stirring speed. Below 65° C. the ingredients of part D are added separately. After cooling down under moderate stirring to 55° C. part C is added. The pH is then checked and adjusted with sodium hydroxide. The mixture is homogenized for 30 sec at 16000 rpm.

Example 8

Every Day Lotion

|  | INCI-Name | % w/w (as supplied) |
|---|---|---|
| Part A | Stearyl Phosphate | 5.00 |
|  | Tricontanyl PVP | 1.00 |
|  | Ethoxydiglycol Oleate | 3.00 |
|  | Squalane | 5.00 |
|  | C12-15 Alkyl Benzoate | 5.00 |
|  | Ethylhexyl Methoxycinnamate | 3.00 |
|  | Glyceryl Stearate | 2.00 |
|  | Cetyl Alcohol | 2.00 |
| Part B | Aqua | 20.00 |
|  | UV-absorber dispersion as described in example 4 | 3.00 |
| Part C | Aqua | qs to 100 |
|  | Steareth-10 Allyl Ether/Acrylates Copolymer | 0.50 |
|  | Glycerin | 2.50 |
|  | Diazolidinyl Urea (and) Iodopropynyl Butylcarbamate | 0.15 |
|  | Sodium Lauroyl Glutamate | 0.70 |
| Part D | Cyclopentasiloxane (and) Dimethiconol | 1.50 |
|  | Triethanolamine | 1.85 |

Manufacturing Instruction:

Part A is prepared by incorporating all ingredients, then stirred under moderate speed and heated to 75° C. Part C is prepared and heated to 75° C. Part C is poured into the part A under moderate stirring. Immediately after the emulsification part B is added, then neutralized with a part of the triethanolamine. The mixture is homogenized for 30 sec. After cooling down under moderate stirring Cyclopentasiloxane (and) Dimethiconol are added. Below 35° C. the pH is checked and adjusted with triethanolamine.

Example 9

Sprayable Sunscreen Emulsion

|  | INCI-Name | % w/w (as supplied) |
|---|---|---|
| Part A | Ceteareth-15 (and) Glyceryl Stearate | 3.00 |
|  | Stearyl Alcohol | 1.00 |
|  | Cetyl Ricinoleate | 0.80 |
|  | Dicaprylyl Ether | 3.00 |
|  | C12-15 Alkyl Benzoate | 3.00 |
|  | Isohexadecane | 2.50 |
|  | Stearyl Dimethicone | 1.00 |
|  | Ethylhexyl Methoxycinnamate | 4.00 |
|  | Cetyl Alcohol | 0.80 |
|  | Di-C12-13 Alkyl Tartrate | 3.00 |
| Part B | Aqua | qs to 100 |
|  | Steareth-10 Allyl Ether/Acrylates Copolymer | 0.45 |
|  | PEG-7 Glyceryl Cocoate | 2.50 |
|  | Glycerin | 2.00 |
|  | Propylene Glycol | 3.00 |
| Part C | Diazolidinyl Urea (and) Iodopropynyl Butylcarbamate | 0.15 |
|  | Aqua | 20.00 |
|  | UV-absorber dispersion as described in example 4 | 12.00 |
|  | Titanium Dioxide (and) Silica (and) Sodium Polyacrylate | 8.00 |
| Part D | Cyclopentasiloxane (and) Dimethiconol | 0.85 |
| Part E | Sodium Hydroxide (and) Water | qs to pH 6.50-7.00 |
| Part F | Fragrance | qs |

Manufacturing Instruction

Part A and part B are heated up to 80° C. Part A is blended into part B under stirring and homogenized with an Ultra Turrax at 11 000 rpm for 30 sec. Part C is heated to 60° C. and added slowly to the emulsion. After cooling down to 40° C. part D is incorporated at room temperature and part E is added.

Example 10

Daily Care Lotion

|  | INCI-Name | % w/w (as supplied) |
|---|---|---|
| Part A | Polyglyceryl Methyl Glucose Distearate | 2.50 |
|  | Cetearyl Alcohol | 2.00 |
|  | Octyl Stearate | 3.00 |
|  | Caprylic/Capric Triglyceride | 4.00 |
|  | Isohexadecane | 4.00 |
|  | Ethylhexyl Methoxycinnamate | 2.70 |

-continued

| | INCI-Name | % w/w (as supplied) |
|---|---|---|
| Part B | Aqua | 64.80 |
| | Glycerin | 5.00 |
| | Phenoxyethanol (and) Methylparaben (and) Butylparaben (and) Ethylparaben (and) Propylparaben | 0.50 |
| | UV-absorber dispersion as described in example 4 | 8.00 |
| Part C | Cyclomethicone (and) Dimethicone | 3.00 |
| Part D | Steareth-10 Allyl Ether/Acrylates Copolymer | 0.50 |

Manufacturing Instruction

Part A and B are heated to 75° C. Part A is added into part B under continuous stirring and homogenized with 11000 rpm for 1 minute. After cooling down to 50° C. part C is added under continuous stirring. After cooling further down to 30° C. part D is added. Afterwards the pH is adjusted between 6.00-6.50.

Example 11

Daily Care with UV Protection

| | INCI-Name | % w/w (as supplied) |
|---|---|---|
| Part A | Glyceryl Stearate SE | 3.00 |
| | Glyceryl Stearate and PEG-100 Stearate | 3.50 |
| | Cetyl Alcohol | 1.50 |
| | Myristyl Myristate | 2.00 |
| | Isopropyl Palmitate | 2.50 |
| | Paraffinum Perliquidum | 5.00 |
| | Octyl Dimethyl PABA | 3.00 |
| Part B | Aqua | qs to 100 |
| | Propylene Glycol | 7.50 |
| | Phenoxyethanol (and) Methylparaben (and) Butylparaben (and) Ethylparaben (and) Propylparaben | 1.00 |
| Part C | Aqua | 30.00 |
| | UV-absorber dispersion as described in example 4 | 10.00 |
| Part D | Sodium Acrylates Copolymer (and) Paraffinium Liquidum (and) PPG-1 Trideceth-6 | 2.00 |
| Part E | Citric Acid | 0.30 |

Manufacturing Instruction:

Part A and B are heated separately to 75° C. After adding part B into part A the mixture is homogenized with Ultra Turrax for one minute at 11000 rpm. After cooling down to 50° C. part C is added. Afterwards the mixture is homogenized for one minute at 16000 rpm. At a temperature <40° C. part D is added. At room temperature the pH-value is adjusted with part E between 6.00 and 6.50.

Example 12

O/W Every Day UV Protection Lotion

| | INCI-Name | % w/w (as supplied) |
|---|---|---|
| Part A | Glyceryl Stearate (and) PEG-100 Stearate | 5.00 |
| | Stearyl Alcohol | 1.00 |
| | Tripalmitin | 0.70 |

-continued

| | INCI-Name | % w/w (as supplied) |
|---|---|---|
| | Dimethicone | 2.00 |
| | C12-15 Alkyl Benzoate | 5.00 |
| | Isopropyl Palmitate | 5.00 |
| | Ethylhexyl Methoxycinnamate | 3.00 |
| Part B | Water | qs to 100 |
| | Polysorbate 60 | 0.50 |
| | Glycerin | 3.00 |
| Part C | Water | 10.00 |
| | UV-absorber dispersion as described in example 4 | 8.00 |
| Part D | Phenoxyethanol (and) Methylparaben (and) Ethylparaben (and) Butylparaben (and) Propylparaben (and) Isobutylparaben | 0.70 |
| | Steareth-10 Allyl Ether/Acrylates Copolymer | 1.50 |
| Part E | Water (and) Sodium Hydroxide | qs |
| | Phenoxyethanol (and) Methylparaben (and) Butylparaben (and) Ethylparaben (and) Propylparaben | 1.00 |
| Part C | Aqua | 30.00 |
| | UV-absorber dispersion as described in example 4 | 10.00 |
| Part D | Sodium Acrylates Copolymer (and) Paraffinium Liquidum (and) PPG-1 Trideceth-6 | 2.00 |
| Part E | Citric Acid | 0.30 |

Manufacturing Instruction:

Part A and B are heated separately to 75° C. After adding part B into part A the mixture is homogenized with Ultra Turrax for one minute at 11000 rpm. After cooling down to 50° C. part C is added. Afterwards the mixture is homogenized for one minute at 16000 rpm. At a temperature <40° C. part D is added. At room temperature the pH-value is adjusted with part E between 6.00 and 6.50.

Example 12

O/W Every Day UV Protection Lotion

| | INCI-Name | % w/w (as supplied) |
|---|---|---|
| Part A | Glyceryl Stearate (and) PEG-100 Stearate | 5.00 |
| | Stearyl Alcohol | 1.00 |
| | Tripalmitin | 0.70 |
| | Dimethicone | 2.00 |
| | C12-15 Alkyl Benzoate | 5.00 |
| | Isopropyl Palmitate | 5.00 |
| | Ethylhexyl Methoxycinnamate | 3.00 |
| Part B | Water | qs to 100 |
| | Polysorbate 60 | 0.50 |
| | Glycerin | 3.00 |
| Part C | Water | 10.00 |
| | UV-absorber dispersion as described in example 4 | 8.00 |
| Part D | Phenoxyethanol (and) Methylparaben (and) Ethylparaben (and) Butylparaben (and) Propylparaben (and) Isobutylparaben | 0.70 |
| | Steareth-10 Allyl Ether/Acrylates Copolymer | 1.50 |
| Part E | Water (and) Sodium Hydroxide | qs |
| Part F | Fragrance | qs |

Manufacturing Instruction:

Part A and B are heated separately up to 75° C., part C is heated to 60° C. Afterwards part B is poured into part A under stirring. The mixture is homogenized with an Ultra Turrax for 30 sec. at 11 000 rpm and part C is incorporated. After cooling down to 40° C. part D is added. At room temperature the pH-value is adjusted with Sodium Hydroxide between 6.30 and 6.70 and part F is added.

Example 13

O/W Every Day UV Protection

|  | INCI-Name | % w/w (as supplied) |
|---|---|---|
| Part A | Glyceryl Stearate (and) PEG-100 Stearate | 5.00 |
|  | Stearyl Alcohol | 1.00 |
|  | Tripalmitin | 0.70 |
|  | Dimethicone | 2.00 |
|  | C12-15 Alkyl Benzoate | 5.00 |
|  | Isopropyl Palmitate | 5.00 |
|  | Ethylhexyl Methoxycinnamate | 3.00 |
| Part B | Water | qs to 100 |
|  | Polysorbate 60 | 0.50 |
|  | Glycerin | 3.00 |
| Part C | Water | 10.00 |
|  | UV-absorber dispersion as described in example 4 | 8.00 |
| Part D | Phenoxyethanol (and) Methylparaben (and) Ethylparaben (and) Butylparaben (and) Propylparaben (and) Isobutylparaben | 0.70 |
|  | Steareth-10 Allyl Ether/Acrylates Copolymer | 1.50 |
| Part E | Water (and) Sodium Hydroxide | qs |
| Part F | Fragrance | qs |

Manufacturing Instruction:

Part A and B are heated separately up to 75° C., part C is heated to 60° C. Afterwards part B is poured into part A under stirring. The mixture is homogenized with an Ultra Turrax for 30 sec. at 11 000 rpm and part C is incorporated. After cooling down to 40° C. part D is added. At room temperature the pH-value is adjusted with Sodium Hydroxide between 6.30 and 6.70 and part F is added.

Example 14

Sunscreen Cream

|  | INCI-Name | % w/w (as supplied) |
|---|---|---|
| Part A | Cetearyl Alcohol (and) Dicetyl Phosphate (and) Ceteth-10 Phosphate | 4.50 |
|  | C12-15 Alkyl Benzoate | 6.00 |
|  | Caprylic/Capric Triglyceride | 7.00 |
|  | Pentaerythritol Tetraisostearate | 2.00 |
|  | Ethylhexyl Methoxycinnamate | 3.00 |
|  | Isoamyl p-Methoxycinnamate | 2.00 |
| Part B | Aqua | qs to 100 |
|  | Glycerin | 2.00 |
|  | Propylene Glycol | 1.50 |
|  | Magnesium Aluminium Silicate | 1.20 |
| Part C | Steareth-10 Allyl Ether/Acrylates Copolymer | 0.50 |
|  | UV-absorber dispersion as described in example 4 | 12.00 |
| Part D | Phenyl Trimethicone | 1.50 |
|  | Phenoxyethanol (and) Methylparaben (and) Butylparaben (and) Ethylparaben (and) Propylparaben | 0.70 |
| Part E | Sodium Hydroxide | 0.90 |

Manufacturing Instruction:

Part A and part B are heated separately to 75° C. Part B is added into part A under continuous stirring and afterwards homogenized with Ultra Turrax for 30 sec at 11000 rpm. After cooling down to 60° C. part C is added. At 40° C. part C is added and homogenized for 15 sec at 11000 rpm. At room temperature the pH-value is adjusted with part E.

Example 15

UVA/UVB Daily Care Lotion, Type O/W

|  | INCI-Name | % w/w (as supplied) |
|---|---|---|
| Part A | Glyceryl Stearate (and) PEG-100 Stearate | 5.00 |
|  | Stearyl Alcohol | 1.00 |
|  | Tripalmitin | 0.70 |
|  | Mineral Oil | 15.00 |
| Part B | Water | qs to 100 |
|  | Polysorbate 60 | 0.50 |
|  | Glycerin | 3.00 |
| Part C | Water | 10.00 |
|  | UV-absorber dispersion as described in example 4 | 8.00 |
| Part D | Steareth-10 Allyl Ether/Acrylates Copolymer | 1.50 |
|  | Phenoxyethanol (and) Methylparaben (and) Ethylparaben (and) Butylparaben (and) Propylparaben (and) Isobutylparaben | 0.70 |
| Part E | Water (and) Sodium Hydroxide | qs |
| Part F | Fragrance | qs |

Manufacturing Instruction:

Part A and B are heated separately to 75° C.; part C to 60° C. Part B is poured into part A under stirring. After one-minute of homogenization at 11000 rpm part C is added to the mixture of A/B. After cooling down to 40° C. part D is incorporated. At room temperature the pH value is adjusted with part E between 6.3 and 7.0. Finally part F is added.

Example 16

UVA/UVB Daily Care Lotion, Type O/W

|  | INCI-Name | % w/w (as supplied) |
|---|---|---|
| Part A | Oleth-3 Phosphate | 0.60 |
|  | Steareth-21 | 2.50 |
|  | Steareth-2 | 1.00 |
|  | Cetyl Alcohol | 0.80 |
|  | Stearyl Alcohol | 1.50 |
|  | Tribehenin | 0.80 |
|  | Isohexadecane | 8.00 |
| Part B | Water | qs to 100 |
|  | Glycerin | 2.00 |
|  | Disodium EDTA | 0.10 |
| Part C | Cyclopentasiloxane | 4.50 |
|  | PEG-12 Dimethicone | 2.00 |
| Part D | Sodium Acrylates Copolymer (and) Mineral Oil (and) PPG-1 Trideceth-6 | 1.50 |
| Part E | UV-absorber dispersion as described in example 4 | 10.00 |
| Part F | Tocopheryl Acetate | 0.45 |
|  | DMDM Hydantoin (and) Iodopropynyl Butylcarbamate (and) Aqua (and) Butylene Glycol | 0.85 |
| Part G | Water (and) Citric Acid | qs |
|  | Fragrance | qs |

Manufacturing Instruction:

Part A and part B are heated separately to 75° C. Part A is poured into part B under stirring. Immediately after the emulsification, part C is added to the mixture and homogenized with an Ultra Turrax at 11000 rpm for 30 sec. After cooling down to 65° C. Sodium Acrylates Copolymer (and) Mineral Oil (and) PPG-1 Trideceth-6 At 50° C. is added slowly to the UV absorber dispersion. At about 35-30° C. part F is incorporated. The pH is adjusted with part G between 5.5 and 6.5.

Example 17

UV-A/UV-B Every Day Protection Lotion O/W

|  | INCI-Name | % w/w (as supplied) |
|---|---|---|
| Part A | Glyceryl Dilaurate | 2.00 |
|  | Ethylhexyl Palmitate | 6.00 |
|  | Cetyl Alcohol | 1.00 |
|  | Glyceryl Stearate | 2.00 |
|  | Laureth-23 | 1.00 |
|  | Isopropyl Palmitate | 2.00 |
|  | Tribehenin | 0.80 |
|  | Beeswax | 1.50 |
|  | Lanolin Oil | 1.00 |
| Part B | Water | qs to 100 |
|  | Propylene Glycol | 4.00 |
|  | Water (and) Titanium Dioxide (and) Alumina (and) Sodium Meta-phosphate (and) Phenoxyethanol (and) Sodium Methylparaben | 4.00 |
| Part C | Steareth-10 Allyl Ether/Acrylates Copolymer | 1.00 |
| Part D | Phenoxyethanol (and) Methylparaben (and) Ethylparaben (and) Butylparaben (and) Propylparaben (and) Isobutylparaben | 1.00 |
|  | UV-absorber dispersion as described in example 4 | 8.00 |
| Part E | Water (and) Sodium Hydroxide | qs |

Manufacturing Instruction:

Part A and part B are heated separately up to 80° C. Part A is poured into part B while stirring and homogenized with an Ultra Turrax by 11000 rpm for 30 sec. After cooling down to 60° C. part C is incorporated. At 40° C. part D is added slowly under continuous stirring. The pH is adjusted with part E between 6.50-7.00.

Example 18

Sprayable Sunscreen Lotion

|  | INCI-Name | % w/w (as supplied) |
|---|---|---|
| Part A | Potassium Cetyl Phosphate | 0.20 |
|  | Isohexadecane | 7.00 |
|  | VP/Eicosene Copolymer | 1.50 |
|  | Di-C12-13 Alkyl Tartrate | 6.00 |
|  | Ethylhexyl Triazone | 2.50 |
|  | C12-15 Alkyl Benzoate | 4.50 |
| Part B | Water | qs to 100 |
|  | Sorbeth-30 | 2.00 |
|  | Sorbitan Stearate (and) Sucrose Cocoate | 4.00 |
|  | Titanium Dioxide (and) Alumina (and) Silica (and) Sodium Polyacrylate | 2.50 |
| Part C | Water | 30.00 |
|  | UV-absorber dispersion as described in example 4 | 12.00 |
| Part D | Phenoxyethanol (and) Methylparaben (and) Ethylparaben (and) Butylparaben (and) Propylparaben (and) Isobutylparaben | 0.70 |
| Part E | Water (and) Citric Acid | qs |

Manufacturing Instruction:

Part A and part B are heated separately up to 80° C., part C is heated to 50° C. Part B is poured into part A and homogenized with an Ultra Turrax for 1 minute at 11000 rpm. After cooling down to 50° C. part C is added under continuous stirring. At 40° C. part D is incorporated and homogenized again for 10 sec. at 11000 rpm. The pH is adjusted with part E.

Example 19

O/W Every Day UV Protection Lotion

|  | INCI-Name | % w/w (as supplied) |
|---|---|---|
| Part A | Glyceryl Stearate (and) PEG-100 Stearate | 5.00 |
|  | Stearyl Alcohol | 1.00 |
|  | Tripalmitin | 0.70 |
|  | Dimethicone | 2.00 |
|  | Caprylic/Capric Triglyceride | 5.00 |
|  | Isopropyl Palmitate | 5.00 |
|  | Ethylhexyl Methoxycinnamate | 3.00 |
| Part B | Water | qs to 100 |
|  | Polysorbate 60 | 0.50 |
|  | Glycerin | 3.00 |
| Part C | Water | 10.00 |
|  | UV-absorber dispersion as described in example 4 | 8.00 |
| Part D | Phenoxyethanol (and) Methylparaben (and) Ethylparaben (and) Butylparaben (and) Propylparaben (and) Isobutylparaben | 0.70 |
|  | Steareth-10 Allyl Ether/Acrylates Copolymer | 1.50 |
| Part E | Water (and) Sodium Hydroxide | qs |
| Part F | Fragrance | qs |

Manufacturing Instruction:

Part A and part B are heated separately up to 75° C., part C is heated to 60° C. Afterwards part B is poured into part A under stirring. The mixture is homogenized with an Ultra Turrax for 30 sec. at 11 000 rpm and part C is incorporated. After cooling down to 40° C. part D is added. At room temperature the pH-value is adjusted with Sodium Hydroxide between 6.30 and 6.70 and part F is added.

Example 20

Water Resistant Sunscreen Emulsion

|  | INCI-Name | % w/w (as supplied) |
|---|---|---|
| Part A | Polyglyceryl-10 Pentastearate (and) Behenyl Alcohol (and) Sodium Stearoyl Lactylate | 2.50 |
|  | VP/Eicosene Copolymer | 1.50 |
|  | Stearyl Alcohol | 1.50 |
|  | Squalane | 4.00 |
|  | C12-15 Alkyl Benzoate | 7.50 |
|  | Octocrylene | 1.50 |
|  | 4-Methylbenzylidene Camphor | 3.00 |
|  | Ethylhexyl Methoxycinnamate | 2.00 |
| Part B | Water | qs to 100 |
|  | Glycerin | 1.80 |
|  | Steareth-10 Allyl Ether/Acrylates Copolymer | 0.80 |
| Part C | UV-absorber dispersion as described in example 4 | 9.00 |
| Part D | VP/Hexadecene Copolymer | 2.70 |
|  | Cyclomethicone | 1.50 |
|  | Phenoxyethanol (and) Methylparaben (and) Ethylparaben (and) Butylparaben (and) Propylparaben (and) Isobutylparaben | 0.70 |
| Part E | Aqua (and) Tocopheryl Acetate (and) Caprylic/Capric Triglyceride (and) Polysorbate 80 (and) Lecithin | 3.50 |

| INCI-Name | % w/w (as supplied) |
|---|---|
| Part F Fragrance | qs |
| Water (and) Sodium Hydroxide | qs |

Manufacturing Instruction:

Part A and part B are heated separately to 80° C. Part A is poured into part B under continuous stirring. Afterwards the mixture is homogenized with an Ultra Turrax at 11 000 rpm for 1 min. After cooling down to 60° C. part C is incorporated. At 40° C. part D is added and the mixture homogenized for a short time again. At 35° C. part E is added and at room temperature Fragrance is added. Finally the pH is adjusted with Sodium Hydroxide.

Example 21

UVA/UVB Sun Protection Lotion, O/W Type

| | INCI-Name | % w/w (as supplied) |
|---|---|---|
| Part A | Potassium Cetyl Phosphate | 2.00 |
| | Tricontanyl PVP | 1.00 |
| | Caprylic/Capric Triglyceride | 5.00 |
| | C12-15 Alkyl Benzoate | 5.00 |
| | Cetearyl Isononanoate | 5.00 |
| | Glyceryl Stearate | 3.00 |
| | Cetyl Alcohol | 1.00 |
| | Dimethicone | 0.10 |
| | Ethylhexyl Methoxycinnamate | 5.00 |
| Part B | Water | qs to 100 |
| | Glycerin | 3.00 |
| Part C | Steareth-10 Allyl Ether/Acrylates Copolymer | 0.50 |
| Part D | UV-absorber dispersion as described in example 4 | 8.00 |
| Part E | Phenoxyethanol (and) Methylparaben (and) Ethylparaben (and) Butylparaben (and) Propylparaben (and) Isobutylparaben | 1.00 |
| Part F | Water (and) Sodium Hydroxide | qs to pH 7.00 |
| Part G | Fragrance | qs |

Manufacturing Instruction:

Part A and part B are heated separately up to 80° C. Part B is poured into part A under moderate stirring. The mixture is homogenized with an Ultra Turrax at 11000 rpm for 1 minute. After cooling down to 70° C. part C is added under stirring. After cooling further down to 50° C. part D is incorporated very slowly. At 40° C. part E is added. At room temperature the pH is adjusted with part F to 7.00 and part G is added.

Example 22

UVA/UVB Sun Protection Lotion, O/W Type

| | INCI-Name | % w/w (as supplied) |
|---|---|---|
| Part A | Potassium Cetyl Phosphate | 2.00 |
| | Tricontanyl PVP | 1.00 |
| | Caprylic/Capric Triglyceride | 5.00 |
| | C12-15 Alkyl Benzoate | 5.00 |
| | Cetearyl Isononanoate | 5.00 |
| | Glyceryl Stearate | 3.00 |
| | Cetyl Alcohol | 1.00 |
| | Dimethicone | 0.10 |
| | Ethylhexyl Methoxycinnamate | 5.00 |
| Part B | Water | qs to 100 |
| | Glycerin | 3.00 |
| Part C | Steareth-10 Allyl Ether/Acrylates Copolymer | 0.50 |
| Part D | UV-absorber dispersion as described in example 4 | 20.00 |
| Part E | Phenoxyethanol (and) Methylparaben (and) Ethylparaben (and) Butylparaben (and) Propylparaben (and) Isobutylparaben | 1.00 |
| Part F | Water (and) Sodium Hydroxide | qs to pH 7.00 |
| Part G | Fragrance | qs |

Manufacturing Instruction:

Part A and part B are heated separately up to 80° C. Part B is poured into part A under moderate stirring. The mixture is homogenized with an Ultra Turrax at 11000 rpm for 1 minute. After cooling down to 70° C. add part C is added under stirring. After cooling further down to 50° C. part D is incorporated very slowly. At 40° C. part E is added. At room temperature the pH is adjusted with part F to 7.00 and part G is added.

Example 23

Sunscreen Lotion

| | INCI-Name | % w/w (as supplied) |
|---|---|---|
| Part A | Cetearyl Alcohol (and) Dicetyl Phosphate (and) Ceteth-10 Phosphate | 4.00 |
| | C12-15 Alkyl Benzoate | 2.00 |
| | Dicaprylyl Ether | 3.00 |
| | Ethoxydiglycol Oleate | 2.00 |
| | Stearic Acid | 1.00 |
| | Ethylhexyl Methoxycinnamate | 3.00 |
| | Sodium Acrylates Copolymer (and) *Glycine Soja* (and) PPG-1 Trideceth-6 | 0.30 |
| | Squalane | 3.50 |
| | VP/Eicosene Copolymer | 2.00 |
| Part B | Water | qs to 100 |
| | UV-absorber dispersion as described in example 4 | 5.00 |
| Part C | Diazolidinyl Urea (and) Iodopropynyl Butylcarbamate | 0.15 |
| | Propylene Glycol | 2.50 |
| | Water | 10.00 |
| Part D | Cyclopentasiloxane (and) Dimethiconol | 2.00 |
| | Ethoxydiglycol | 5.00 |
| | Cyclopentasiloxane (and) Dimethicone/Vinyl Dimethicone Crosspolymer | 2.00 |
| Part E | Aqua (and) Sodium Hydroxide | qs |
| Part F | Fragrance | qs |

Manufacturing Instruction

Part A and part B are heated separately up to 75° C. Part B is poured into part A under progressive stirring speed. At a temperature <65° C. the ingredients of part D are added separately. After cooling down to 55° C. under moderate stirring part C is added. At a temperature <35° C. the pH is checked and adjusted with Sodium Hydroxide and homogenized with an Ultra Turrax for 30 sec. at 11 000 rpm. Part F is added at room temperature.

Example 24

W/O Sunscreen Lotion

|  | INCI-Name | % w/w (as supplied) |
|---|---|---|
| Part A | PEG-7 Hydrogenated Castor Oil | 3.00 |
|  | Polyglyceryl-3 Diisostearate | 4.00 |
|  | Microcrystalline Wax | 1.00 |
|  | Magnesium Stearate | 1.50 |
|  | Propylparaben | 0.10 |
|  | Mineral Oil | 15.00 |
|  | Octyldodecanol | 8.00 |
|  | Ethylhexyl Triazone | 1.00 |
|  | Ethylhexyl Methoxycinnamate | 2.00 |
| Part B | Water | qs to 100 |
|  | Water (and) Citric Acid | 0.05 |
|  | Methylparaben | 0.15 |
|  | Magnesium Sulfate | 0.50 |
| Part C | UV-absorber dispersion as described in example 4 | 9.00 |
|  | Fragrance | qs |

Manufacturing Instruction:

Part A is heated to 80° C. whilst stirring. Part B is added into part A and homogenized with an Ultra Turrax at 11 000 rpm for one minute. After cooling down to 30° C. part C is incorporated.

Example 25

Skin Protection Sunscreen Lotion W/O

|  | INCI-Name | % w/w (as supplied) |
|---|---|---|
| Part A | Polyglyceryl-2 Dipolyhydroxystearate | 3.00 |
|  | Glyceryl Oleate | 3.00 |
|  | Cetearyl Isononanoate | 7.00 |
|  | Hexyl Laurate | 6.00 |
|  | Dicaprylyl Ether | 6.00 |
|  | Propylparaben | 0.10 |
|  | Hexyldecanol | 3.00 |
|  | Magnesium Stearate | 1.00 |
|  | Beeswax | 1.00 |
|  | Ethylhexyl Methoxycinnamate | 4.00 |
| Part B | Water | qs to 100 |
|  | Methylparaben | 0.15 |
|  | Magnesium Sulfate | 1.00 |
| Part C | UV-absorber dispersion as described in example 4 | 6.00 |

Manufacturing Instruction:

Part A is heated separately to 80° C. under gentle stirring. Part B is added to part A and homogenized for one minute at 11000 rpm. After cooling down to 30° C. part C is added under continuous stirring.

Example 26

O/W Emulsion

|  | INCI-Name | % w/w (as supplied) |
|---|---|---|
| Part A | UV absorber of formula (MC10) | 3 g |
|  | sesame oil | 10 g |
|  | glyceryl stearate | 4 g |
|  | stearic acid | 1 g |
|  | cetyl alcohol | 0.5 g |
|  | polysorbate 20 | 0.2 g |
| Part B | propylene glycol | 4 g |
|  | propylparaben | 0.05 g |
|  | methylparaben | 0.15 g |
|  | triethanolamine | 0.1 g |
|  | carbomer 934 | 0.1 g |
|  | water | ad 100 ml |

Preparation of the Emulsion

Phase (A):

Firstly, the UV absorber is dissolved in sesame oil. The other components of (A) are added thereto and combined.

Phase (B):

Propylparaben and methylparaben are dissolved in propylene glycol. 60 ml of water are then added, heating to 70° C. is carried out and then carbomer 934 is emulsified therein.

Emulsion:

(A) is slowly added to (B) with vigorous application of mechanical energy. The volume is adjusted to 100 ml by the addition of water.

Example 27

Daily Care Cream, Type O/W

|  | INCI name | % w/w (as used) |
|---|---|---|
| Part A | Glyceryl stearate (and) cetearyl alcohol (and) cetyl palmitate (and) cocoglycerides | 4.0 |
|  | Ceteareth-12 | 4.0 |
|  | Cetearyl alcohol | 2.0 |
|  | Dicaprylyl ether | 4.5 |
|  | Ethylhexyl stearate | 4.0 |
|  | Hexyl laurate | 3.5 |
|  | Ethylhexyl triazone | 1.0 |
|  | Benzylidene malonate polysiloxane | 2.0 |
|  | HDI/trimethylol hexyl-lactone crosspolymer (and) silica | 5.0 |
|  | Stearyl dimethicone | 1.0 |
|  | Dimethicone | 2.0 |
|  | Cetyl alcohol | 0.8 |
|  | compound of formula (MC10) | 2.0 |
| Part B | Water | q.s. to 100 |
|  | Water (and) scleroglucan (and) phenoxyethanol | 2.0 |
|  | Glycerol | 2.0 |
| Part C | Steareth-10 allyl ether/acrylate copolymer | 0.45 |
|  | Phenoxyethanol (and) methylparaben (and) ethylparaben (and) butylparaben (and) propylparaben (and) isobutylparaben | 0.7 |

-continued

| | INCI name | % w/w (as used) |
|---|---|---|
| Part D | Aqua (and) tocopheryl acetate (and) caprylic/capric triglyceride (and) polysorbate 80 (and) lecithin | 4.0 |
| Part E | Water (and) sodium hydroxide | q.s. |
| | Fragrance | q.s. |

Preparation Procedure:

Part A and part B are heated separately to 80° C. Part A is poured into part B, whilst stirring continuously. Afterwards the mixture is homogenized with an Ultra Turrax at 11 000 rpm for 20 sec. The mixture is cooled to 60° C. and part C is added. At a temperature below 30° C., part D is added and the pH value is adjusted with sodium hydroxide to between 6.5 and 7.0. Finally, fragrance is added.

Example 28

Sun-Protection Cream, Type O/W

| | INCI name | % w/w (as used) |
|---|---|---|
| Part A | Polyglyceryl-3 methylglucose distearate | 2.0 |
| | Decyl oleate | 5.7 |
| | Isopropyl palmitate | 5.8 |
| | Caprylic/capric triglyceride | 6.5 |
| | compound of formula (MC10) | 2.0 |
| | Ethylhexyl methoxycinnamate | 5.0 |
| | Cetyl alcohol | 0.7 |
| Part B | Glycerol | 3.0 |
| | Carbomer | 0.3 |
| | Water | q.s. to 100 |
| Part C | Phenoxyethanol (and) methylparaben (and) ethylparaben (and) butylparaben (and) propylparaben (and) isobutylparaben | 0.5 |
| Part D | Methylene bis-benzotriazolyl tetramethylbutylphenol (and) aqua (and) decyl glucoside (and) propylene glycol (and) xanthan gum | 8.0 |
| | Water | 20.0 |
| Part E | Water (and) sodium hydroxide | q.s. |
| | Fragrance | q.s. |

Preparation Procedure

Part A and part B are heated separately to 75° C. Part A is poured into part B whilst stirring. The mixture is homogenised with an Ultra Turrax at 11 000 rpm for 15 sec. The mixture is cooled to 60° C. and part C and part D are incorporated. The mixture is homogenised again for a short time (5 sec./11 000 rpm) and further cooled, with moderate stirring. At room temperature, the pH is adjusted with sodium hydroxide solution to between 5.5 and 6.0. Finally, fragrance is added.

Example 29

Daily Care UV-Protection Lotion

| | INCI name | % w/w (as used) |
|---|---|---|
| Part A | Oleth-3 phosphate | 0.6 |
| | Steareth-21 | 2.5 |
| | Steareth-2 | 1.0 |
| | Cetyl alcohol | 0.8 |
| | Stearyl alcohol | 1.5 |
| | Tribehenin | 0.8 |
| | Isohexadecane | 8.0 |
| | compound of formula (MC10) or (MC37) | 5.0 |
| Part B | Water | q.s. to 100 |
| | Glycerol | 2.0 |
| | Methylene bis-benzotriazolyl tetramethylbutylphenol (and) aqua (and) decyl glucoside (and) propylene glycol (and) xanthan gum | 3.0 |
| | Disodium EDTA | 0.1 |
| Part C | Water | 20.0 |
| | Diazolidinyl urea (and) iodopropynyl butylcarbamate | 0.15 |
| | Propylene glycol | 4.0 |
| Part D | Sodium acrylate copolymer (and) liquid paraffin (and) PPG-1 trideceth-6 | 1.5 |
| | Cyclopentasiloxane | 4.5 |
| | PEG-12 dimethicone | 2.0 |
| | Tocopheryl acetate | 0.45 |
| | Water (and) citric acid | q.s. |
| Part E | Fragrance | q.s. |

Preparation Procedure

Heat part A and part B separately to 75° C. Pour part A into part B, whilst stirring continuously. Immediately after emulsification, incorporate in the mixture SF 1202 and SF 1288 from part D. Afterwards homogenise with an Ultra Turrax at 11 000 rpm for 30 sec. Allow to cool to 65° C. and incorporate SALCARE® SC91. At a temperature below 50° C., add part C. At 35° C. or below, incorporate vitamin E acetate and subsequently adjust the pH with citric acid. At room temperature, add part E.

Example 30

Sun-Protection Cream, Type O/W

| | INCI name | % w/w (as used) |
|---|---|---|
| Part A | Polyglyceryl-3 methylglucose distearate | 2.0 |
| | Decyl oleate | 5.7 |
| | Isopropyl palmitate | 5.8 |
| | Caprylic/capric triglyceride | 6.5 |
| | compound of formula (MC14) or (MC37) | 2.0 |
| | Ethylhexyl methoxycinnamate | 5.0 |
| | Cetyl alcohol | 0.7 |
| Part B | Glycerol | 3.0 |
| | Carbomer | 0.3 |
| | Water | q.s. to 100 |
| Part C | Phenoxyethanol (and) methylparaben (and) ethylparaben (and) butylparaben (and) propylparaben (and) isobutylparaben | 0.5 |
| Part D | Methylene bis-benzotriazolyl tetramethylbutylphenol (and) aqua (and) decyl glucoside (and) propylene glycol (and) xanthan gum | 8.0 |
| | Water | 20.0 |
| Part E | Water (and) sodium hydroxide | q.s. |
| | Fragrance | q.s. |

Preparation Procedure:

Part A and part B are heated separately to 75° C. Part A is poured into part B whilst stirring. The mixture is homogenised with an Ultra Turrax at 11 000 rpm for 15 sec. The mixture is cooled to 60° C., and part C and part D are incorporated. The mixture is homogenised again for a short time (5 sec./11 000 rpm). After further cooling, with moderate stirring, the pH is adjusted with sodium hydroxide at room temperature. A solution between pH 5.50 and 6.00 is obtained. Finally, fragrance is added.

Example 31

Sun-Protection Cream, Type O/W

| | INCI name | % w/w (as used) |
|---|---|---|
| Part A | Polyglyceryl-3 methylglucose distearate | 2.0 |
| | Decyl oleate | 5.7 |
| | Isopropyl palmitate | 5.8 |
| | Caprylic/capric triglyceride | 6.5 |
| | Mixture of the compound of formula (MC10) (50%) or (MC37) (50%) and Uvinul A Plus CAS Reg. No. 302776-68-7 (50%) | 2.0 |
| | Ethylhexyl methoxycinnamate | 5.0 |
| | Cetyl alcohol | 0.7 |
| Part B | Glycerol | 3.0 |
| | Carbomer | 0.3 |
| | Water | q.s. to 100 |
| Part C | Phenoxyethanol (and) methylparaben (and) ethylparaben (and) butylparaben (and) propylparaben (and) isobutylparaben | 0.5 |
| Part D | Methylene bis-benzotriazolyl tetramethylbutylphenol (and) aqua (and) decyl glucoside (and) propylene glycol (and) xanthan gum | 8.0 |
| | Water | 20.0 |
| Part E | Water (and) sodium hydroxide | q.s. |
| | Fragrance | q.s. |

Preparation Procedure:

Part A and part B are heated separately to 75° C. Part A is poured into part B whilst stirring. The mixture is homogenised with an Ultra Turrax at 11 000 rpm for 15 sec. After cooling 60° C., part C and part D are incorporated. The mixture is homogenised again for a short time (5 sec./11 000 rpm). After further cooling, with moderate stirring, the pH is adjusted at room temperature with sodium hydroxide solution to between 5.50 and 6.00. Finally, fragrance is added.

Example 32

Sun-Protection Cream, Type O/W

| | INCI name | % w/w (as used) |
|---|---|---|
| Part A | Polyglyceryl-3 methylglucose distearate | 2.0 |
| | Decyl oleate | 5.7 |
| | Isopropyl palmitate | 5.8 |
| | Caprylic/capric triglyceride | 6.5 |
| | Mixture of compound of formula (MC10) (50%) or (MC37) (50%) and benzylidene camphor, CAS Reg. No. 36861-47-9 (50%) | 2.0 |
| | Ethylhexyl methoxycinnamate | 5.0 |
| | Cetyl alcohol | 0.7 |
| Part B | Glycerol | 3.0 |
| | Carbomer | 0.3 |
| | Water | q.s. to 100 |
| Part C | Phenoxyethanol (and) methylparaben (and) ethylparaben (and) butylparaben (and) propylparaben (and) isobutylparaben | 0.5 |
| Part D | Methylene bis-benzotriazolyl tetramethylbutylphenol (and) aqua (and) decyl glucoside (and) propylene | 8.0 |

-continued

| | INCI name | % w/w (as used) |
|---|---|---|
| | glycol (and) xanthan gum | |
| | Water | 20.0 |
| Part E | Water (and) sodium hydroxide | q.s. |
| | Fragrance | q.s. |

Preparation Procedure

Part A and part B are heated separately to 75° C. Part A is poured into part B whilst stirring. The mixture is homogenised with an Ultra Turrax at 11 000 rpm for 15 sec. After cooling to 60° C., part C and part D are incorporated. The mixture is homogenised again for a short time (5 sec./11 000 rpm). After further cooling, with moderate stirring, the pH is adjusted at room temperature with sodium hydroxide. A solution between pH 5.50 and 6.00 is obtained. Finally, fragrance is added.

What is claimed is:

1. A method of protecting human and animal hair and skin from UV radiation comprising, applying thereto a compound of formula

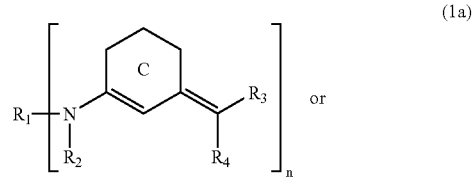

(1a)

or

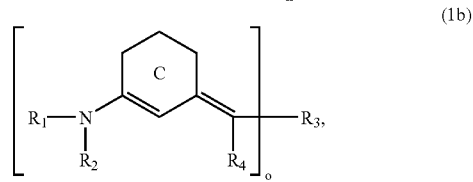

(1b)

wherein
$R_2$ is hydrogen; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl; or a cyano group;
$R_4$ is a cyano group; or -$Q_1$-$R_5$;
$Q_1$ is —COO—; —CONH—; —CO—; —SO$_2$—; or —CONR$_6$—;
$R_5$ is $C_1$-$C_{22}$alkyl; cyclo-$C_3$-$C_8$alkyl; or unsubstituted or $C_1$-$C_6$alkyl-substituted $C_6$-$C_{20}$aryl;
$R_6$ is hydrogen; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl;
the cyclohexene radical C is not substituted or substituted by one or more $C_1$-$C_5$alkyl;
n is from 2 to 4;
o is from 2 to 4;
if n=2, in formula (1a)
$R_1$ is an alkylene, cycloalkylene or phenylene-radical; or $R_1$ and $R_2$ simultaneously form a cycloalkylene or phenylene radical; and
$R_3$ is a cyano group or -$Q_1$-$R_5$; or $R_3$ and $R_4$ together form a 5- to 7-membered, monocyclic carbocyclic ring, which is optionally interrupted by —O— or —NR$_7$—;

If o=2, in formula (1b)

$R_3$ is an alkylene, cycloalkylene or phenylene radical, which is optionally substituted with $C_1$-$C_4$alkyl, $C_1$-$C_4$alkoxy, —$COR_6$, —$COOR_6$ or —$CONHR_6$; and $R_1$ is hydrogen; a cyano group; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl; or $R_1$ and $R_2$ together with the nitrogen atom linking them form a —$(CH_2)_m$— ring which is optionally interrupted by —O— or by —$NR_7$—;

$R_7$ is hydrogen; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl;

m is a number from 3 to 7;

if n=3, in formula (1a)

$R_1$ is a trivalent alkyl group, which is optionally interrupted by one or more —O— or —$NR_7$-groups; and $R_3$ is a cyano group or -$Q_1$-$R_5$; or $R_3$ and $R_4$ together form a 5- to 7-membered, monocyclic carbocyclic ring;

if o=3, in formula (1b)

$R_3$ is an alkylidene, cycloalkylidene or phenylidene radical; and $R_1$ is hydrogen; a cyano group; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl; or $R_1$ and $R_2$ together with the nitrogen atom linking them form a —$(CH_2)_m$— ring which is optionally interrupted by —O— or by —$NR_7$—;

if n=4, in formula (1a)

$R_1$ is a tetravalent alkyl group; and $R_3$ is a cyano group; or -$Q_1$-$R_5$; or $R_3$ and $R_4$ together form a 5- to 7-membered, monocyclic carbocyclic ring;

if n=4, in formula (1b)

$R_3$ is a tetravalent alkyl group; and $R_1$ is hydrogen; a cyano group; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl; or $R_1$ and $R_2$ together with the nitrogen atom linking them form a —$(CH_2)_m$— ring which is optionally interrupted by —O— or by —$NR_7$—.

2. A method according to claim 1, wherein in formula (1a)

$R_1$ is defined as in formula (1a);

$R_2$ is hydrogen;

$R_3$ is a cyano group;

$R_4$ is —$CONHR_5$; and $R_5$ is $C_1$-$C_{22}$alkyl; or $C_6$-$C_{20}$aryl.

3. A method according to claim 1, wherein if n=2, compounds of formula

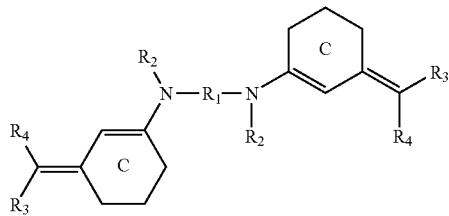

are used, wherein $R_1$ is a *—$(CH_2)_m$—* group, not substituted or substituted with one or more than one $C_1$-$C_5$radicals; a bivalent radical of formula

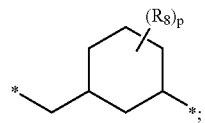

a bivalent radical of formula

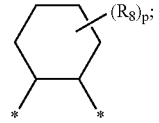

or $R_1$ and $R_2$ together with the 2 linking nitrogen atoms form a bivalent radical of formula

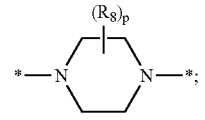

$R_8$ is hydrogen; or $C_1$-$C_5$alkyl;

$R_3$ is a cyano group; or -$Q_1$-$R_5$;

p is a number form 0 to 3;

the cyclohexene radical C is not substituted or substituted by one or more $C_1$-$C_5$alkyl; and $R_2$ is hydrogen; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl; or a cyano group;

$R_4$ is a cyano group; or -$Q_1$-$R_5$;

$Q_1$ is —COO—; —CONH—; —CO—; —$SO_2$—; or —$CONR_6$—;

$R_5$ is $C_1$-$C_{22}$alkyl; cyclo-$C_3$-$C_8$alkyl; or unsubstituted or $C_1$-$C_6$alkyl-substituted $C_6$-$C_{20}$aryl; and $R_6$ is hydrogen; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl.

4. A method according to claim 1, wherein compounds of formula

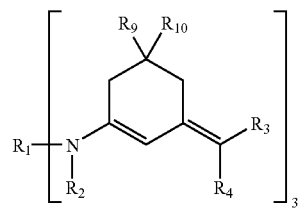

are used, wherein $R_1$ is a trivalent radical of formula

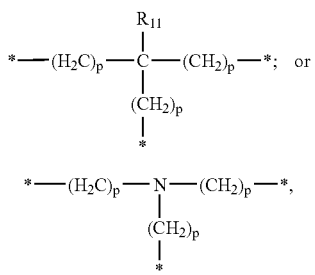

$R_2$ is hydrogen; or $C_1$-$C_5$alkyl;
$R_3$ and $R_4$, independently from each other are a cyano group; or -$Q_1$-$R_5$;
$Q_1$ is —COO—; —CONH—; —CO—; —$SO_2$—; —$CONR_{12}$—;
$R_5$ is $C_1$-$C_5$alkyl;
$R_9$ and $R_{10}$ independently from each other are $C_1$-$C_4$alkyl;
$R_{11}$ and $R_{12}$ independently from each other are hydrogen; or $C_1$-$C_5$alkyl; and
p is a number from 0 to 5.

5. A method according to claim 1, wherein compounds of formula

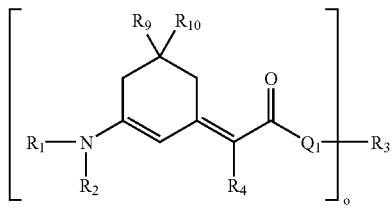

are used, wherein
$R_1$ and $R_2$ are each independently of the other $C_1$-$C_{22}$alkyl; or a cyano group; or $R_1$ and $R_2$ together with the nitrogen atom linking them form a —$(CH_2)_m$—ring which is optionally interrupted by —O— or by —$NR_7$—;
$R_4$ is a cyano group; or -$Q_1$-$R_5$;
o is 3; or 4;
if o=3
$R_2$ is a trivalent alkyl radical;
if o=4
$R_2$ is a tetravalent alkyl radical;
$Q_1$ is —COO—; —CONH—; —CO—; —$SO_2$—; or —$CONR_6$—;
$R_5$ is $C_1$-$C_{22}$alkyl; cyclo-$C_3$-$C_8$alkyl; or unsubstituted or $C_1$-$C_6$alkyl-substituted $C_6$-$C_{20}$aryl;
$R_6$ is hydrogen; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl;
m is a number from 3 to 7;
$R_7$ is hydrogen; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl;
and
$R_9$ and $R_{10}$ independently from each other are $C_1$-$C_4$alkyl.

6. A method according to claim 1, wherein an additional UV absorber is used.

7. A method according to claim 6 wherein the additional UV absorber is selected from the triazine compounds of formula

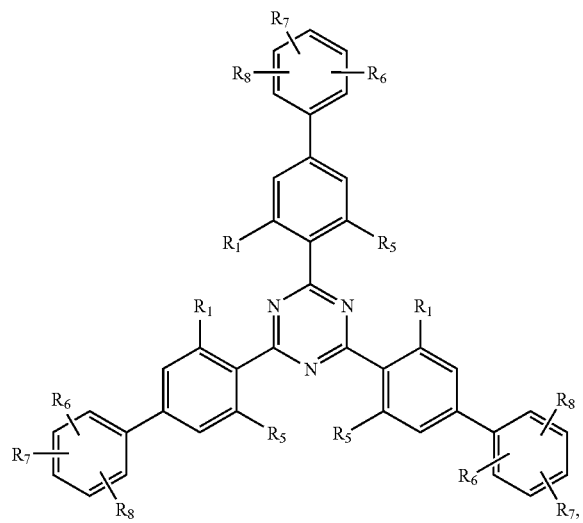

wherein
$R_1$ and $R_5$ are hydrogen; $C_1$-$C_{18}$alkyl; or $C_6$-$C_{12}$aryl; and
$R_6$, $R_7$ and $R_8$, independently from each other are hydrogen; hydroxy; halogen; $C_1$-$C_{18}$alkyl; $C_1$-$C_{18}$alkoxy; $C_6$-$C_{12}$aryl; biphenylyl; $C_6$-$C_{12}$aryloxy; $C_1$-$C_{18}$alkylthio; carboxy; —COOM; $C_1$-$C_{18}$-alkylcarboxyl; aminocarbonyl; or mono- or di-$C_1$-$C_{18}$alkylamino; $C_1$-$C_{10}$acylamino; or —COOH.

8. A method according to claim 6, wherein a UV filter combination comprising
($t_3$) the compound of formula

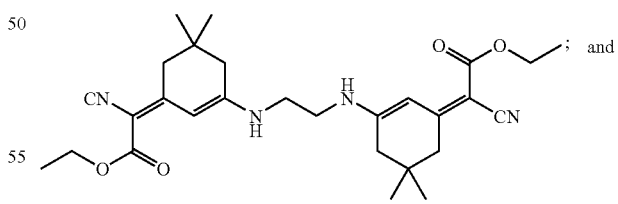

($t_4$) 1,3,5-Triazine, 2,4,6-tris[1,1'-biphenyl]-4-yl-(9CI) is used.

9. A method of protecting human and animal hair and skin from UV radiation comprising, applying thereto a momomeric, oligomeric or polymeric compound comprising structural elements of formula

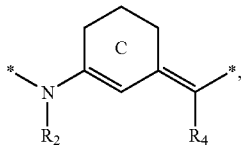 (2)

wherein
- at least one of the asterix-marked radicals may be bound to the momomeric, oligomeric or polymeric radical;
- the cyclohexene radical C is not substituted or substituted by one or more $C_1$-$C_5$alkyl; and
- $R_2$ is hydrogen; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl; or a cyano group;
- $R_4$ is a cyano group; or -$Q_1$-$R_5$;
- $Q_1$ is —COO—; —CONH—; —CO—; —$SO_2$—; or —$CONR_6$—;
- $R_5$ is $C_1$-$C_{22}$alkyl; cyclo-$C_3$-$C_8$alkyl; or unsubstituted or $C_1$-$C_6$alkyl-substituted $C_6$-$C_{20}$aryl; and
- $R_6$ is hydrogen; $C_1$-$C_{22}$alkyl; cyclo-$C_3$-$C_8$alkyl; unsubstituted or $C_1$-$C_6$alkyl- or $C_1$-$C_6$alkoxy-substituted $C_6$-$C_{20}$aryl.

10. A method according to claim 9, wherein the momomeric, oligomeric or polymeric compound corresponds to formula

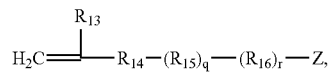 (3)

wherein
- Z is a radical of formula (2);
- $R_{13}$ is hydrogen; halogen; or $C_1$-$C_5$alkyl;
- $R_{14}$ is —CONH—; —COO—; or a phenylene radical;
- $R_{15}$ is $C_1$-$C_{20}$alkylene; or $C_6$-$C_{20}$arylene;
- $R_{16}$ is —COO—; —OCO—; —CONH—; —NH—CO—O—; —NH—CO—; —$SO_2$NH—; —NH$SO_2$—; —$SO_2$— or —O—;
- q is 0; or an integer; and
- r is 0; or an integer.

11. A cosmetic preparation comprising at least one or more compounds of formula (1a), or (1b) according to claim 1 with cosmetically acceptable carriers or adjuvants.

* * * * *